US012268895B2

(12) United States Patent
Olcott et al.

(10) Patent No.: US 12,268,895 B2
(45) Date of Patent: *Apr. 8, 2025

(54) JOINT OPTIMIZATION OF RADIONUCLIDE AND EXTERNAL BEAM RADIOTHERAPY

(71) Applicant: RefleXion Medical, Inc., Hayward, CA (US)

(72) Inventors: Peter Demetri Olcott, Los Gatos, CA (US); Michael Kirk Owens, North Easton, MA (US); Debashish Pal, Sunnyvale, CA (US)

(73) Assignee: RefleXion Medical, Inc., Hayward, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 18/301,085

(22) Filed: Apr. 14, 2023

(65) Prior Publication Data

US 2023/0405359 A1    Dec. 21, 2023

Related U.S. Application Data

(63) Continuation of application No. 17/158,848, filed on Jan. 26, 2021, now Pat. No. 11,654,300.

(Continued)

(51) Int. Cl.
*A61N 5/10* (2006.01)

(52) U.S. Cl.
CPC ......... *A61N 5/1031* (2013.01); *A61N 5/1039* (2013.01); *A61N 5/1045* (2013.01);
(Continued)

(58) Field of Classification Search
CPC ...... A61N 5/10; A61N 5/1031; A61N 5/1039; A61N 5/1045; A61N 5/1001; A61N 5/103;
(Continued)

(56) References Cited

U.S. PATENT DOCUMENTS

| 4,932,412 A | 6/1990 | Goldenberg |
|---|---|---|
| 5,647,663 A | 7/1997 | Holmes |

(Continued)

FOREIGN PATENT DOCUMENTS

| CN | 1824342 A | 8/2006 |
|---|---|---|
| CN | 101496018 A | 7/2009 |

(Continued)

OTHER PUBLICATIONS

Extended European Search Report mailed on May 31, 2024, for EP Application No. 23 211 269.8, filed on Jun. 22, 2018, 5 pages.

(Continued)

*Primary Examiner* — Jurie Yun
(74) *Attorney, Agent, or Firm* — Cooley LLP

(57) ABSTRACT

Disclosed herein are methods for radiotherapy treatment plan optimization for irradiating one or more target regions using both an internal therapeutic radiation source (ITRS) and an external therapeutic radiation source (ETRS). One variation of a method comprises iterating through ITRS radiation dose values and ETRS radiation dose values to attain a cumulative dose that meets prescribed dose requirements. In some variations, an ITRS is an injectable compound that has a targeting backbone and a radionuclide, and images acquired using an imaging compound that has the same targeting backbone as the injectable compound can be used to calculate the radiation dose deliverable using the injectable ITRS, and also to calculate firing filters for delivering radiation using a biologically-guided radiation therapy (BGRT) system. Image data acquired from a previous treatment session may be used to adapt the dose provided by an ITRS and/or ETRS for a future treatment session.

28 Claims, 13 Drawing Sheets

Related U.S. Application Data

(60) Provisional application No. 62/966,997, filed on Jan. 28, 2020.

(52) U.S. Cl.
CPC .............. *A61N 2005/1024* (2013.01); *A61N 2005/1034* (2013.01); *A61N 2005/1098* (2013.01)

(58) Field of Classification Search
CPC .. A61N 5/1038; A61N 5/1047; A61N 5/1067; A61N 2005/1024; A61N 2005/1034; A61N 2005/1098; A61N 2005/1021; A61N 2005/1052; A61N 2005/1054
See application file for complete search history.

(56) References Cited

U.S. PATENT DOCUMENTS

| | | |
|---|---|---|
| 6,187,037 B1 | 2/2001 | Satz |
| 6,438,202 B1 | 8/2002 | Olivera et al. |
| 6,714,620 B2 | 3/2004 | Caflisch et al. |
| 6,911,200 B2 | 6/2005 | Yu et al. |
| 8,663,083 B2 | 3/2014 | Georgi et al. |
| 8,693,629 B2 | 4/2014 | Sgouros et al. |
| 8,784,846 B2 | 7/2014 | Schulte et al. |
| 9,155,909 B2 | 10/2015 | Ishikawa |
| 9,180,214 B1 | 11/2015 | Miao |
| 9,198,989 B2 | 12/2015 | Keyak et al. |
| 9,320,813 B2 | 4/2016 | Peyman |
| 9,340,524 B2 | 5/2016 | Chen et al. |
| 9,387,342 B2 | 7/2016 | Prionas et al. |
| 9,387,344 B2 | 7/2016 | Sgouros et al. |
| 9,597,427 B2 | 3/2017 | Keyak et al. |
| 9,757,084 B2 | 9/2017 | Sgouros et al. |
| 9,803,025 B2 | 10/2017 | Hettmann et al. |
| 9,925,283 B2 | 3/2018 | Weichert et al. |
| 9,956,428 B2 | 5/2018 | Kelly |
| 10,007,961 B2 | 6/2018 | Grudzinski et al. |
| 10,456,600 B2 | 10/2019 | Owens et al. |
| 10,521,563 B2 | 12/2019 | Von Busch et al. |
| 10,674,983 B2 | 6/2020 | Black |
| 10,688,320 B2 | 6/2020 | Voronenko et al. |
| 10,918,884 B2 | 2/2021 | O'Connor et al. |
| 11,033,757 B2 | 6/2021 | Voronenko et al. |
| 11,633,626 B2 | 4/2023 | Voronenko et al. |
| 11,648,418 B2 | 5/2023 | Owens et al. |
| 11,654,300 B2 | 5/2023 | Olcott et al. |
| 2002/0137991 A1 | 9/2002 | Scarantino et al. |
| 2004/0018968 A1 | 1/2004 | Sgouros et al. |
| 2004/0096033 A1 | 5/2004 | Seppi et al. |
| 2004/0115203 A1 | 6/2004 | Dadachova et al. |
| 2005/0027196 A1 | 2/2005 | Fitzgerald |
| 2005/0143965 A1 | 6/2005 | Failla et al. |
| 2005/0196340 A1 | 9/2005 | Holash et al. |
| 2005/0207531 A1 | 9/2005 | Dempsey et al. |
| 2005/0238578 A1 | 10/2005 | Fritzberg et al. |
| 2006/0159220 A1 | 7/2006 | Heuscher |
| 2006/0228297 A1 | 10/2006 | Larsen et al. |
| 2006/0257317 A1 | 11/2006 | Bigner et al. |
| 2006/0257369 A1 | 11/2006 | Kessler et al. |
| 2007/0093432 A1 | 4/2007 | Yang |
| 2008/0193377 A1 | 8/2008 | Line et al. |
| 2008/0230705 A1 | 9/2008 | Rousso et al. |
| 2008/0247996 A1 | 10/2008 | Yu et al. |
| 2009/0054720 A1 | 2/2009 | Sgouros et al. |
| 2009/0117044 A1 | 5/2009 | Hengerer et al. |
| 2010/0054411 A1 | 3/2010 | Nord et al. |
| 2010/0086183 A1 | 4/2010 | Vik et al. |
| 2010/0150309 A1 | 6/2010 | Nord et al. |
| 2010/0178244 A1 | 7/2010 | Arnsdorf et al. |
| 2010/0178245 A1 | 7/2010 | Arnsdorf et al. |
| 2011/0086850 A1 | 4/2011 | Ang et al. |
| 2011/0122997 A1 | 5/2011 | Lu et al. |
| 2011/0135058 A1 | 6/2011 | Sgouros et al. |
| 2011/0163238 A1 | 7/2011 | Teshigawara et al. |
| 2011/0291015 A1 | 12/2011 | Mazin |
| 2012/0292534 A1 | 11/2012 | Geneser et al. |
| 2012/0323599 A1 | 12/2012 | Bal et al. |
| 2013/0083004 A1 | 4/2013 | Nord et al. |
| 2013/0188856 A1 | 7/2013 | Adler, Jr. et al. |
| 2014/0005464 A1 | 1/2014 | Bharat et al. |
| 2014/0252227 A1 | 9/2014 | Sasai et al. |
| 2014/0275704 A1 | 9/2014 | Zhang et al. |
| 2014/0343344 A1 | 11/2014 | Saunders et al. |
| 2015/0031988 A1 | 1/2015 | Takeuchi et al. |
| 2015/0043709 A1 | 2/2015 | Shapiro et al. |
| 2015/0050349 A1 | 2/2015 | Schulte et al. |
| 2015/0161338 A1 | 6/2015 | Scherrer et al. |
| 2015/0196665 A1 | 7/2015 | Govindan et al. |
| 2015/0196666 A1 | 7/2015 | Govindan et al. |
| 2015/0202319 A1 | 7/2015 | Govindan et al. |
| 2015/0251017 A1 | 9/2015 | De Crevoisier et al. |
| 2016/0038767 A1 | 2/2016 | Wiersma et al. |
| 2016/0074541 A1 | 3/2016 | Zalutsky et al. |
| 2016/0213949 A1 | 7/2016 | Uhlemann et al. |
| 2016/0256713 A1 | 9/2016 | Saunders et al. |
| 2016/0287903 A1 | 10/2016 | Sgouros et al. |
| 2016/0361566 A1 | 12/2016 | Larkin et al. |
| 2017/0014642 A1 | 1/2017 | An et al. |
| 2017/0028220 A1 | 2/2017 | Schulte et al. |
| 2017/0087385 A1 | 3/2017 | Miettinen et al. |
| 2017/0186153 A1 | 6/2017 | Enderling et al. |
| 2017/0327567 A1 | 11/2017 | Skokos et al. |
| 2018/0015154 A1 | 1/2018 | Weichert et al. |
| 2018/0021461 A1 | 1/2018 | Weichert et al. |
| 2018/0126012 A1 | 5/2018 | Weichert et al. |
| 2018/0133518 A1 | 5/2018 | Harper et al. |
| 2018/0273634 A1 | 9/2018 | Tran et al. |
| 2018/0345042 A1 | 12/2018 | Voronenko et al. |
| 2018/0369611 A1 | 12/2018 | Owens et al. |
| 2019/0114765 A1 | 4/2019 | Enderling et al. |
| 2019/0118001 A1 | 4/2019 | Mazin et al. |
| 2019/0209731 A1 | 7/2019 | Keyak et al. |
| 2019/0218621 A1 | 7/2019 | Davicioni et al. |
| 2019/0262451 A1 | 8/2019 | Kelly |
| 2019/0381338 A1 | 12/2019 | Voronenko et al. |
| 2020/0016283 A1 | 1/2020 | Cuthbertson |
| 2020/0023088 A1 | 1/2020 | Tsai et al. |
| 2023/0356003 A1 | 11/2023 | Voronenko et al. |
| 2023/0390580 A1 | 12/2023 | Owens et al. |

FOREIGN PATENT DOCUMENTS

| | | |
|---|---|---|
| CN | 102068763 A | 5/2011 |
| CN | 102641561 A | 8/2012 |
| CN | 103180014 A | 6/2013 |
| CN | 103845068 A | 6/2014 |
| CN | 104284697 A | 1/2015 |
| CN | 104866928 A | 8/2015 |
| CN | 104994909 A | 10/2015 |
| CN | 105658279 A | 6/2016 |
| CN | 106563211 A | 4/2017 |
| EP | 3 539 616 A1 | 9/2019 |
| JP | 2002-522128 A | 7/2002 |
| JP | 2012-035072 A | 2/2012 |
| JP | 2014-023741 A | 2/2014 |
| JP | 2014-527439 A | 10/2014 |
| JP | 2016-168077 A | 9/2016 |
| JP | 2017-500165 A | 1/2017 |
| JP | 2018-007875 A | 1/2018 |
| WO | WO-00/76556 A2 | 12/2000 |
| WO | WO-00/76556 A3 | 12/2000 |
| WO | WO-03/088954 A1 | 10/2003 |
| WO | WO-2005/052721 A2 | 6/2005 |
| WO | WO-2005/052721 A3 | 6/2005 |
| WO | WO-2005/117542 A2 | 12/2005 |
| WO | WO-2005/117542 A3 | 12/2005 |
| WO | WO-2006/012355 A2 | 2/2006 |
| WO | WO-2006/012355 A3 | 2/2006 |
| WO | WO-2006/119285 A1 | 11/2006 |
| WO | WO-2008/057363 A2 | 5/2008 |
| WO | WO-2008/057363 A3 | 5/2008 |
| WO | WO-2008/068717 A2 | 6/2008 |

(56) References Cited

FOREIGN PATENT DOCUMENTS

| | | |
|---|---|---|
| WO | WO-2008/068717 A3 | 6/2008 |
| WO | WO-2008/079569 A2 | 7/2008 |
| WO | WO-2008/079569 A3 | 7/2008 |
| WO | WO-2008/130380 A2 | 10/2008 |
| WO | WO-2008/130380 A3 | 10/2008 |
| WO | WO-2009/018383 A1 | 2/2009 |
| WO | WO-2009/031073 A2 | 3/2009 |
| WO | WO-2009/031073 A3 | 3/2009 |
| WO | WO-2010/018477 A2 | 2/2010 |
| WO | WO-2010/018477 A3 | 2/2010 |
| WO | WO-2010/083107 A1 | 7/2010 |
| WO | WO-2010/121153 A2 | 10/2010 |
| WO | WO-2010/121153 A3 | 10/2010 |
| WO | WO-2013/054788 A1 | 4/2013 |
| WO | WO-2013/096776 A2 | 6/2013 |
| WO | WO-2013/096776 A3 | 6/2013 |
| WO | WO-2015/153991 A1 | 10/2015 |
| WO | WO-2015/168431 A1 | 11/2015 |
| WO | WO-2015/179858 A1 | 11/2015 |
| WO | WO-2016/023786 A1 | 2/2016 |
| WO | WO-2016/064750 A1 | 4/2016 |
| WO | WO-2017/133654 A1 | 8/2017 |
| WO | WO-2017/197259 A1 | 11/2017 |
| WO | WO-2018/017526 A1 | 1/2018 |
| WO | WO-2018/022571 A1 | 2/2018 |
| WO | WO-2018/053648 A1 | 3/2018 |
| WO | WO-2019/008040 A1 | 1/2019 |
| WO | WO-2019/094657 A1 | 5/2019 |
| WO | WO-2019/174979 A1 | 9/2019 |
| WO | WO-2019/217928 A1 | 11/2019 |

OTHER PUBLICATIONS

Geets, X. et al. (Oct. 2007). "Adaptive biological image-guided IMRT with anatomic and functional imaging in pharyngo-laryngeal tumors: impact on target volume delineation and dose distribution using helical tomotherapy," Radiother. Oncol. 85(1):105-115.

Guohua, H. et al. (Nov. 2002). "Chapter 8: Radionuclide diagnosis and treatment," in Bladder Tumor, Shanghai: Tongji University Press, first edition, first printing, p. 41 (with English Translation).

Hongsheng, S. (Aug. 2015). "Chapter 8: Nuclear medicine imaging," in Practical Imaging Diagnosis, Xi'an Jiaotong University Press, first edition, first printing, p. 167 (with English Translation).

Non-Final Office Action mailed on Jun. 24, 2024, for U.S. Appl. No. 18/295,448, filed Apr. 4, 2023, 8 pages.

Notice of Allowance mailed on Sep. 29, 2024, for U.S. Appl. No. 18/295,448, filed Apr. 4, 2023, 5 pages.

Peng, C. et al. (Jun. 2016). "Chapter 15: Clinical radiotherapy technique," in Clinical Diagnosis and Treatment of Oncological Diseases, published by Jilin Science and Technology Press, first edition, first printing, p. 276 (with English translation).

Shiying, Y. (Jul. 2009). "Chapter 4: Design of radiotherapy plan," in Guidelines for Standardized Diagnosis and Treatment of Tumors, published by Huazhong University of Science and Technology Press, first edition, first printing, p. 106 (with English translation).

Xuening, Z. (Dec. 2010). "Chapter 2: Principles and Stereotactic Techniques of LEKSELL Gamma Knife," in Gamma Knife Surgery for Intracranial Disease-Clinical Imaging, published by Tianjin Science and Technology Press, first edition, first printing, pp. 29-30 (with English Translation).

Zhiliao, Z. et al. (Mar. 2002). "Progress in Physics of Tumor Radiotherapy," Beijing Medical University and China Union Medical University Joint Publishing House, first edition, first printing, pp. 163-164 (with English translation).

Adaptive Radiation Therapy: ISBN:9781439816356. 2011. CRC Press. X Allen Li (Ed.): 426 pages (cover only); URL: https://www.google.com/books/edition/Adaptive_Radiation_Therapy/9hEPvAlgPfMC (accessed Aug. 31, 2021).

Besse, I.M. et al. (2009). "Modeling Combined Radiopharmaceutical Therapy: A Linear Optimization Framework," Tech. in Cancer Res. and Treatment 8:51-60.

Chen, X. et al. (2012). "Smoothing proximal gradient method for general structured sparse regression," The Annals of Applied Statistics 6:719-752.

Corrected Notice of Allowability mailed on Mar. 13, 2023, for U.S. Appl. No. 17/235,812, filed Apr. 20, 2021, 4 pages.

Croteau, E. et al. (2016)."PET Metabolic Biomarkers for Cancer," Biomark Cancer. 8(Suppl 2):61-69.

Divgi, C. et al. (2021). "Overcoming Barriers to Radiopharmaceutical Therapy (RPT): An Overview From the NRG-NCI Working Group on Dosimetry of Radiopharmaceutical Therapy," Int. J. Radiation Oncol. Biol. Phys. 109:905-912.

Extended European Search Report mailed on Oct. 15, 2019, for European Application No. 17 764 132.1, filed on Mar. 9, 2017, 4 pages.

Extended European Search Report mailed on Feb. 3, 2021, for EP Application No. 18 810 297.4, filed on May 30, 2018, 4 pages.

Extended European Search Report mailed on Jun. 14, 2021, for EP Application No. 18 821 003.3, filed on Jun. 22, 2018, 5 pages.

Final Office Action mailed on May 18, 2022, for U.S. Appl. No. 16/016,272, filed Jun. 22, 2018, 31 pages.

Fredriksson (2013). "Robust optimization of radiation therapy accounting for geometric uncertainty," KTH Engin. Sciences, pp. 8-14.

Hurwitz, M. (2006). "Combined External Beam Radiotherapy and Brachytherapy for the Management of Prostate Cancer," Radiation Oncology, pp. 29-32.

International Search Report mailed on Jun. 27, 2017, for PCT Patent Application No. PCT/US2017/021647, filed on Mar. 9, 2017, 3 pages.

International Search Report mailed on Nov. 16, 2018, for PCT Application No. PCT/US2018/039104, filed on Jun. 22, 2018, 4 pages.

International Search Report mailed on Oct. 3, 2018, for PCT Application No. PCT/US2018/035188, filed on May 30, 2018, 4 pages.

International Search Report mailed on May 6, 2021, for PCT Application No. PCT/US2021/015119, filed on Jan. 26, 2021, 8 pages.

James, S.S. et al. (2021). "Current Status of Radiopharmaceutical Therapy," Int. J. Radiation Oncol. Biol. Phys. 109:891-901.

Kim et al. "18F-FDG PET/CT of Advanced Gastric Carcinoma and Association of H ER2 Expression with Standardized Uptake Value." Asia Oceania J Nucl Med Biol, 2014; 2(1): 12-18.

Kong et al. "Effect of Midtreatment PET/CT-Adapted Radiation Therapy with Concurrent Chemotherapy in Patients with Locally Advanced Non-Small-Cell Lung Cancer." JAMA Oncol. Oct. 2017; 3(10): 1358-1365. Published online Oct. 12, 2017. Prepublished online Jun. 1, 2017.

Lassmann, M. et al. (2018). "The Relevance of Dosimetry in Precision Medicine," J. Nuclear Med. 59:1494-1499.

Mayer, R. et al. (1998). "CT-simulator based brachytherapy planner: seed localization and incorporation of biological considerations," Radiat. Oncol. Investig. 6:35-51.

National Cancer Institute (2020). "Radiopharmaceuticals: Radiation therapy enters the molecular age," 5 total pages.

Non-Final Office Action mailed on Dec. 6, 2019, for U.S. Appl. No. 15/993,325, filed May 30, 2018, 8 pages.

Non-Final Office Action mailed on Jun. 26, 2020, for U.S. Appl. No. 16/122,735, filed Sep. 5, 2018, 16 pages.

Non-Final Office Action mailed on Dec. 22, 2020, for U.S. Appl. No. 16/554,258, filed Aug. 28, 2019, 11 pages.

Non-Final Office Action mailed on Sep. 21, 2021, for U.S. Appl. No. 16/016,272, filed Jun. 22, 2018, 34 pages.

Non-Final Office Action mailed on Jul. 7, 2022, for U.S. Appl. No. 17/158,848, filed Jan. 26, 2021, 21 pages.

Non-Final Office Action mailed on Aug. 30, 2022, for U.S. Appl. No. 17/235,812, filed Apr. 20, 2021, 8 pages.

Non-Final Office Action mailed on Nov. 21, 2022, for U.S. Appl. No. 16/016,272, filed Jun. 22, 2018, 27 pages.

Notice of Allowance mailed on Dec. 11, 2020, for U.S. Appl. No. 16/122,735, filed Sep. 5, 2018, 10 pages.

Notice of Allowance mailed on Apr. 20, 2020, for U.S. Appl. No. 15/993,325, filed May 30, 2018, 7 pages.

(56) References Cited

OTHER PUBLICATIONS

Notice of Allowance mailed on Apr. 2, 2021, for U.S. Appl. No. 16/554,258, filed Aug. 28, 2019, 7 pages.
Notice of Allowance mailed on Jan. 31, 2023, for U.S. Appl. No. 17/158,848, filed Jan. 26, 2021, 9 pages.
Notice of Allowance mailed on Feb. 1, 2023, for U.S. Appl. No. 17/235,812, filed Apr. 20, 2021, 7 pages.
Notice of Allowance mailed on Mar. 9, 2023, for U.S. Appl. No. 16/016,272, filed Jun. 22, 2018, 8 pages.
O'Doherty, J. (2015). "A review of 3D image-based dosimetry, technical considerations and emerging perspectives in $^{90}$Y microsphere therapy," J. Diagnostic Imaging in Therapy 2:1-34.
St. James, S. (2021). "Current Status of Radiopharmaceutical Therapy," Int. J. Radiation Oncol. Biol. Phys. 109:891-901.
Thorek, D. "Positron lymphography: multimodal, high-resolution, dynamic mapping and resection of lymph nodes after X intradermal injection of 18F-FDG." J Nucl Med. Sep. 2012;53(9):1438-45.
Thorwarth, D. et al. (2010). "Physical radiotherapy treatment planning based on functional PET/CT data," Radiotherapy Oncology, pp. 317-324.
Tuncel, N. "Adaptive radiotherapy from past to future frontiers." International Journal of Radiology & Radiation Therapy 2021; 8(2):81-84.
Xiao, Y. et al. (2021). "Toward Individualized Voxel-Level Dosimetry for Radiopharmaceutical Therapy," Int. J. Radiation Oncol. Biol. Phys. 109:902-904.
Written Opinion of the International Searching Authority mailed on Jun. 27, 2017, for PCT Patent Application No. PCT/US2017/021647, filed on Mar. 9, 2017, 5 pages.
Written Opinion of the International Searching Authority mailed on Nov. 16, 2018, for PCT Application No. PCT/US2018/039104, filed on Jun. 22, 2018, 6 pages.
Written Opinion of the International Searching Authority mailed on Oct. 3, 2018, for PCT Application No. PCT/US2018/035188, filed on May 30, 2018, 28 pages.
Written Opinion of the International Searching Authority mailed on May 6, 2021, for PCT Application No. PCT/US2021/015119, filed on Jan. 26, 2021, 9 pages.
Yan, D. et al. (1997). "Adaptive radiation therapy," *Physics Med. Biol.* 42:123-132.
Zhang, H. et al. (2002). Progress in the Physics of Tumor Radiation Therapy, Beijing Medical University, China Union Medical University Joint Press, p. 164 (with English translation).
Zhao, H. et al. (2015). Practical Imaging Diagnosis, University Press, Aug. 2015, p. 167 (with English translation).

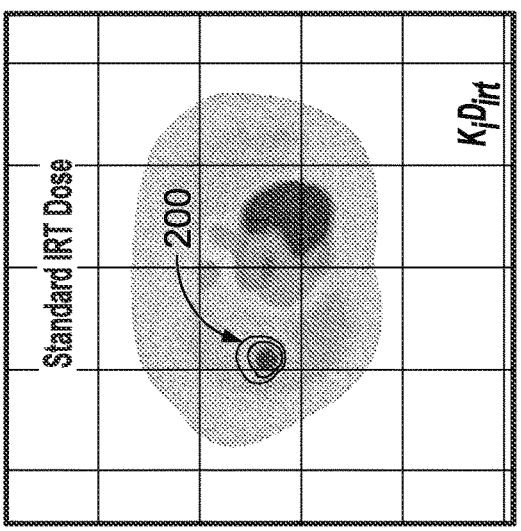
FIG. 2A
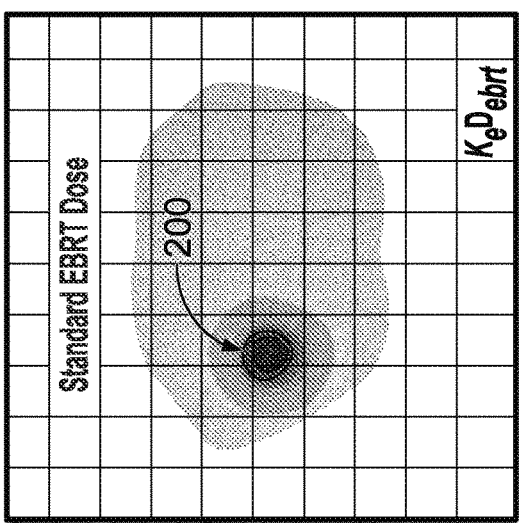
FIG. 2B
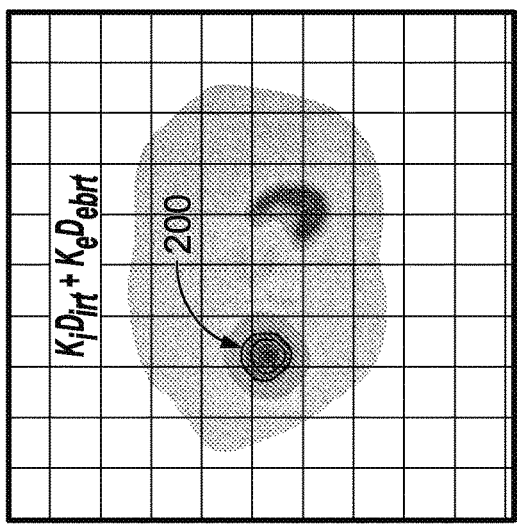
FIG. 2C
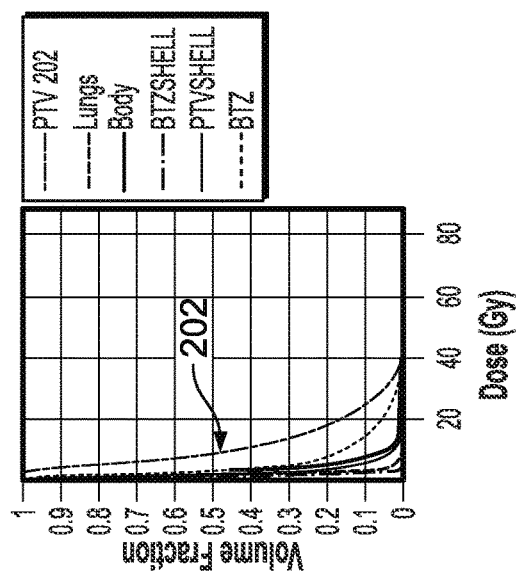
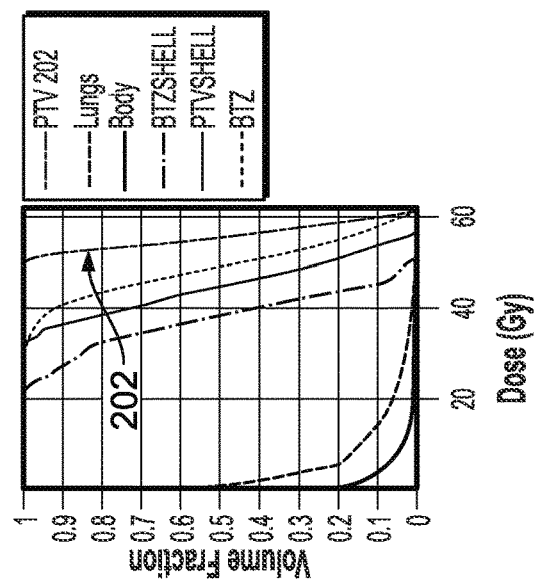
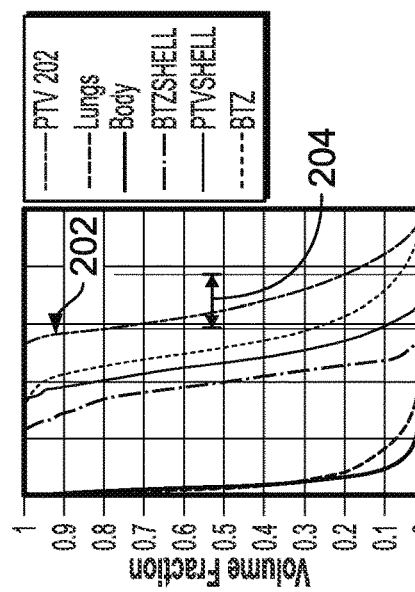

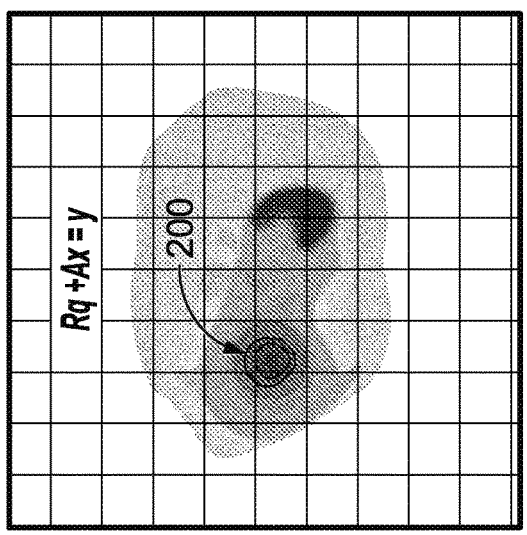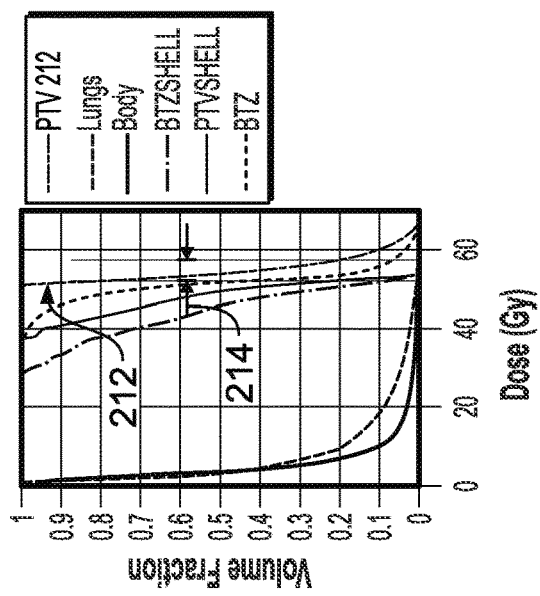
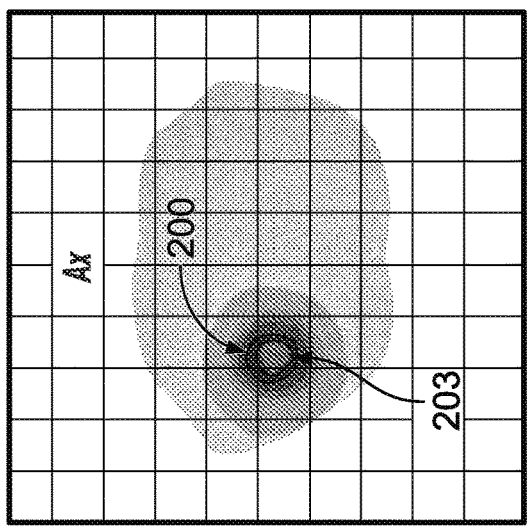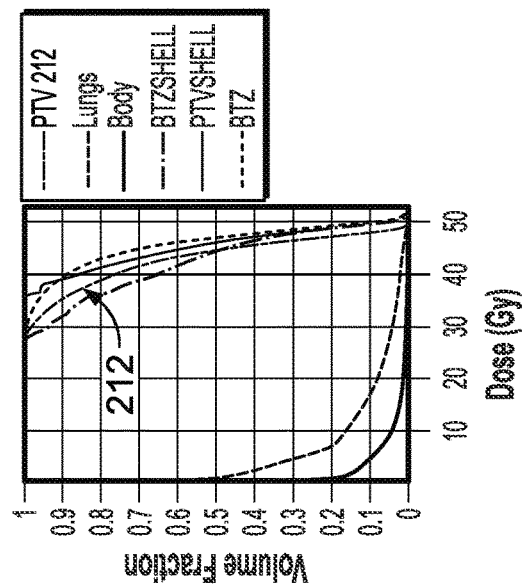
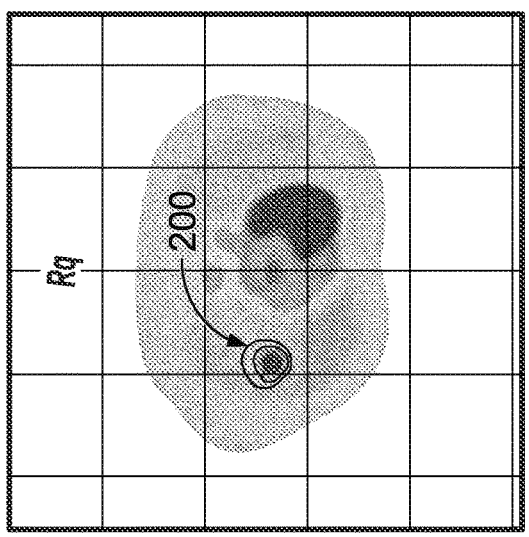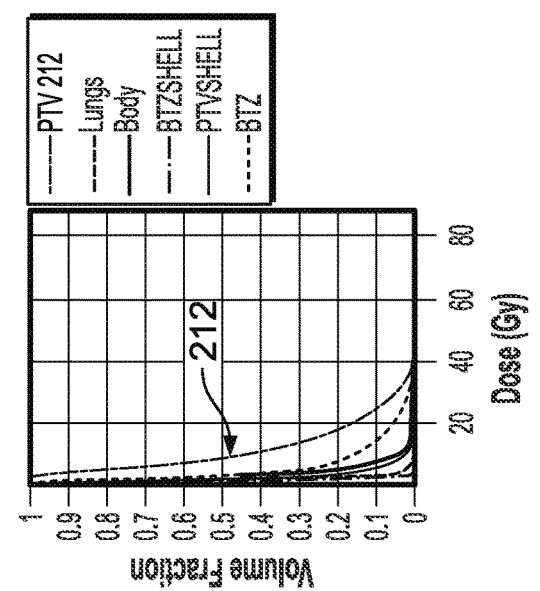
FIG. 5C  FIG. 5D  FIG. 5E

| Imaging/Diagnostic Compound | Therapeutic Compound |
|---|---|
| Ga-68-DOTA-TATE (NETSPOT), Cu-64-DOTA-TATE | Lu-177-DOTA-TATE (Lutathera) |
| Ga-68-DOTA-TOC, Tb-149-DOTA-TOC, Tb-152-DOTA-TOC, Cu-64-DOTA-TOC | Lu-177-DOTA-TOC, Y-90-DOTA-TOC, Bi-213-DOTA-TOC, Tb-149-DOTA-TOC |
| RN1-PSMA-11, RN1-PSMA-617, RN1-I&T where RN1 = Ga-68, Cu-64, Zr-89, Sc-44, F-18 | Lu-177-PSMA-617, Ac-225-PSMA-617, Y-90-PSMA-617 |
| F-18-PSMA-7.3, Zr-89-J591, Cu-64-RPS-085/072, Ga-68-RPS-085/072 | RN2-PSMA-i&T, RN2-PSMA-7.3, RN2-AI-J591, where RN2 = Lu-177, Ac-225, At-211, BAY2315497 (Th-227-PSMA-TTC), Cu-67-RPS-085/072 |
| Ga-68-NeoBOMB1 | Lu-177-NeoBOMB1 |
| Ga-68-Pentixafor | Lu-177-Pentixafor |
| I-123-MIBG | I-131-MIBG |
| Zr-89-TCMC trastuzumab | Pb-212-TCMC trastuzumab |
| Tc-99m-MDP, Tc-99m-(X) | Ra-223-Chloride, Rh-188-(X)W |
| I-123-Iodide | I-131-Iodide |
| I-123-Iobenguane | I-131-Iobenguane |
| In-111-Ibritumomab tiuxetan | Y-90-Ibritumomab tiuxetan |
| Cu-64-SARTATE, Cu-64-(X) | Cu-67-SARTATE, Cu-64-(X) |
| NaF-18 | Radium-223 |
| Zr-89-Girentuximab, Cu-64-Girentuximab | RN2-Girentuximab, where RN2 = Lu-177, Ac-225, At-211 |
| RN4-MSLN Ab, where RN4 = In-111, Zr-89, Cu-64 | BAY2287411 (Th-MSLN-TTC-227) |
| RN3-FAPI-x, where RN3 = Ga-68, Cu-64, Zr-89, Sc-44, FAIF-18, x = 02, 04, 34, 46, 74. RN3-FAP-2286, where RN3 = Ga-68, Cu-68, Zr-89, Sc-44, FAIF-18 | RN-FAPI-x, where RN = Lu-177, Ac-225, At-211, Pb-212, Bi-213, x = 02, 04, 34, 46, 74. RN5-FAP-2286, where RN5 = Lu-177, Ac-225, At-211, Pb-212, Bi-213 |
| F-18-5F7 | Astatine-211-5F7 |
| In-111-DTPA nanobody | Lu-177-DTPA nanobody |

FIG. 8

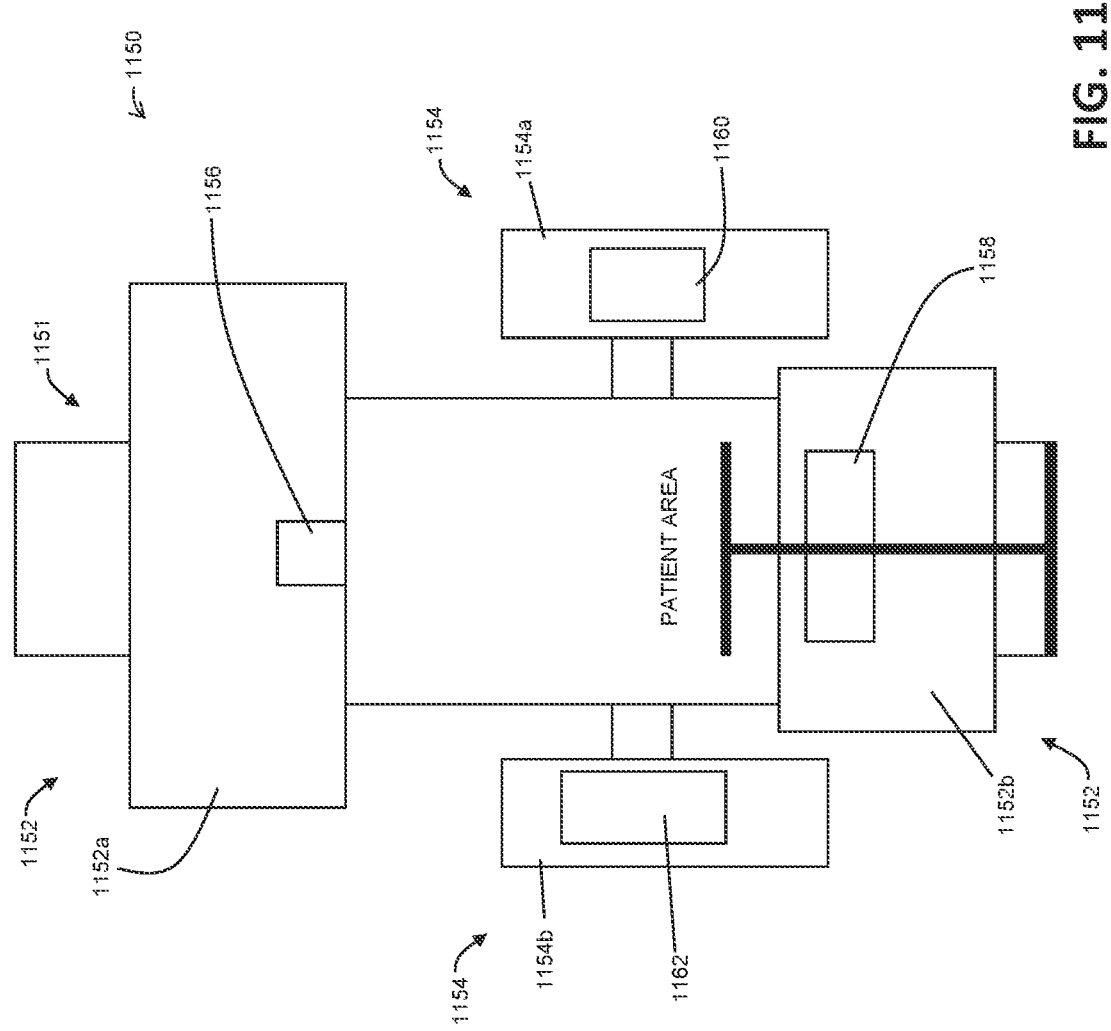

JOINT OPTIMIZATION OF RADIONUCLIDE AND EXTERNAL BEAM RADIOTHERAPY

CROSS-REFERENCE TO RELATED APPLICATIONS

This application is a continuation of U.S. patent application Ser. No. 17/158,848, filed Jan. 26, 2021, which claims priority to U.S. Provisional Patent Application No. 62/966,997, filed Jan. 28, 2020, the content of which is hereby incorporated by reference in their entirety.

BACKGROUND

Radiation provided by an external therapeutic radiation source (ETRS), such as a high-energy photon or particle source, may be able to deliver a prescribed dose of radiation to a tumor (e.g., lesion). For example, external beam radiation therapy (EBRT) having one or more therapeutic radiation sources can be precisely targeted to solid tumors in the body based on pre-treatment images. A highly homogenous dose can be delivered to solid tumors to help control the spread of many kinds of cancer. Unfortunately, many cancers are not visible on pre-treatment images, therefore, EBRT may not be able to provide a complete cure for widely disseminated (e.g., metastatic) and/or microscopic disease. While EBRT may be effective for visible solid tumors, radiation provided by an internal therapeutic radiation source (ITRS), such as a radioactive compound that is injected or implanted into the patient, may be able to address diffuse or widely disseminated and/or micro-metastatic and/or microscopic disease, as well as solid tumors.

One example of radiotherapy provided by an internal therapeutic radiation source (ITRS) is internal radionuclide therapy. Internal radionuclide therapy (IRT) typically involves the injection of a radionuclide and/or a radiopharmaceutical compound into a patient, which results in the systemic distribution of the radionuclide and/or radiopharmaceutical compound throughout the patient's body. Radionuclides are radioactive isotopes, and some radionuclides target tumor cells directly. A radiopharmaceutical compound may comprise a radionuclide attached to a carrier molecule (e.g., a targeting backbone) that selectively binds to cancer cells. A radiopharmaceutical compound can accumulate in tumors and their surrounding cells and may also attach to microscopic tumors. The radioactive decay of an isotope at the site of accumulation of a radiopharmaceutical creates ionization of the local region that may destroy cancer cells directly, adjacent tumor cells through a crossfire effect, or the surrounding cells that support the tumor. However, non-specific uptake of the radionuclide and/or radiopharmaceutical in healthy tissues can be toxic to the patient, especially when the radiopharmaceutical accumulates in organs such as the bone marrow, bladder, liver, kidney, spleen, salivary glands, and the lacrimal glands. This toxicity limits the maximum injectable dose of radionuclide and/or radiopharmaceutical, and therefore may limit the effectiveness of IRT. In addition, for larger tumors, the IRT dose distribution tends to be heterogeneous; that is, for larger tumors, the dose tends to be more highly concentrated in the center of the tumor but decreases rapidly toward the outer boundaries of the tumor. For example, the radionuclide Lu-177 has a maximum beta range in water of approximately 1.5 mm. For tumors larger than 1 cm, the radiation dose peaks significantly in the center of the tumor but falls off rapidly toward the edge of the tumor. If insufficient dose is delivered to the edge/boundary regions of the tumor, then these boundary cells can survive, and the cancer may recur.

Some radiotherapy methods have combined both IRT and ERT modalities. In these methods, each modality is optimized independently and then summed together. Some methods may apply a linear scaling factor in an effort to attain a desired dose distribution. However, because the doses of IRT and ERT modalities are simply summed, the resultant cumulative dose distribution is still heterogeneous. Accordingly, improved methods of multi-modal radiotherapy are desirable.

SUMMARY

Disclosed herein are systems and methods for generating a joint radiotherapy treatment plan that jointly optimizes for both the radiation dose provided by an internal therapeutic radiation source (ITRS) and the radiation dose provided by an external therapeutic radiation source (ETRS).

One variation of a method for generating a joint internal and external radiotherapy treatment plan may comprise calculating a radiation dose ($D_{0\_ITRS}$) deliverable using an internal therapeutic radiation source (ITRS), calculating a radiation dose ($D_{0\_ETRS}$) deliverable using an external therapeutic radiation source (ETRS), adjusting the radiation dose ($D_{0\_ITRS}$) deliverable using the ITRS and/or the radiation dose ($D_{0\_ETRS}$) deliverable using the ETRS to attain a cumulative radiation dose ($D_{cumulative}$) that meets prescribed dose requirements to a patient target region, and generating a radiotherapy treatment plan that specifies a radiation dose to be delivered using the ITRS ($D_{ITRS}$) and/or a radiation dose to be delivered using the ETRS ($D_{ETRS}$) such that $D_{ITRS}+D_{ETRS}=D_{cumulative}$. $D_{cumulative}$ may be a biologically equivalent dose (BED). Calculating the radiation dose ($D_{0\_ITRS}$) deliverable using the ITRS may use functional image data of a patient, which may optionally comprise anatomical data. Functional image data may comprise PET image data. The PET image data may be acquired during a previous treatment session. In some variations, functional image data may comprise imaging data acquired using a compound comprising a radionuclide, such as a radionuclide is selected from a group consisting of NaF-18, F-18, Ga-68, Cu-64, Zr-89, I-124, Sc-44, Tb-152, Y-86, Tc-99m, In-111, Tb-155, I-123, Cu-67, Sr-89, Y-90, I-131, Tb-161, Lu-177, Bi-212, Bi-213, At-211, Ac-225, Th-227, Ra-223, Pb-212, and Tb-149. Calculating the radiation dose ($D_{0\_ITRS}$) deliverable using the ITRS may comprise calculating a ITRS dose-mapping matrix (R) that maps a radiation dose to a plurality of patient regions resulting from applying a quantity of ITRS (q) to the patient, where $D_{0\_ITRS}=Rq$. The ITRS may be a compound comprising a targeting backbone and a radionuclide, and the dose-mapping matrix (R) may be calculated using functional image data acquired using a diagnostic imaging compound comprising the ITRS targeting backbone. Alternatively, or additionally, the ITRS may be a compound comprising a targeting backbone and a radionuclide, and the dose-mapping matrix (R) may be calculated using functional image data acquired using a diagnostic imaging compound comprising the ITRS radionuclide. The calculation of the radiation dose ($D_{0\_ITRS}$) may use Monte-Carlo dose calculation methods, voxel-based S-value kernels, and/or convolution using a Dose-Volume-Kernel. Calculating the radiation dose ($D_{0\_ETRS}$) deliverable using the ETRS may use functional image data of a patient, which may optionally comprise anatomical image data. Functional image data may comprise PET image data.

In some variations, calculating the radiation dose ($D_{0\_ETRS}$) deliverable using the ETRS may use anatomical image data. Calculating the radiation dose ($D_{0\_ETRS}$) deliverable using the ETRS may comprise calculating a ETRS dose-mapping matrix (A) that maps a radiation dose to a plurality of patient regions resulting from applying a radiation fluence (x) to the patient, where $D_{0\_ETRS}=Ax$. Calculating the radiation dose ($D_{0\_ITRS}$) deliverable using the ITRS may use a first set of functional image data acquired using a first compound comprising a first targeting backbone and a first radionuclide, and calculating the radiation dose ($D_{0\_ETRS}$) deliverable using the ETRS may use a second set of functional image data acquired using a second compound comprising a second targeting backbone and a second radionuclide. The first targeting backbone and the second targeting backbone may be the same, and/or the first radionuclide and the second radionuclide may be the same. Calculating the radiation dose ($D_{0\_ITRS}$) deliverable using the ITRS may use a first set of functional image data acquired using a first compound comprising a first targeting backbone and a first radionuclide, and the ITRS may be a second compound comprising a second targeting backbone and a second radionuclide. The first targeting backbone and the second targeting backbone may be the same, and/or the first radionuclide and the second radionuclide may be the same.

In some variations, the ITRS may be a first compound comprising a first targeting backbone and a first radionuclide, and the ETRS may be a radiotherapy system comprising a high-energy radiation source movable about a patient. The radiotherapy system may comprise a plurality of PET detectors and may be configured to apply therapeutic radiation to the patient based on positron annihilation emission data acquired by the PET detectors. Some methods may comprise injecting a PET tracer into the patient, and the PET tracer may comprise a second targeting backbone that is the same as the first targeting backbone of the ITRS.

Adjusting the radiation dose the radiation dose ($D_{0\_ITRS}$) deliverable using the ITRS and/or the radiation dose ($D_{0\_ETRS}$) deliverable using the ETRS may comprise iterating through different values of the ITRS radiation dose ($D_{0\_ITRS}$) in conjunction with iterating through different values of the ETRS radiation dose ($D_{0\_ETRS}$) to meet one or more dose constraints. The one or more dose constraints may comprise one or more cost functions, and the method may comprise iterating through different values of the ITRS radiation dose ($D_{0\_ITRS}$) and/or different values of the ETRS radiation dose ($D_{0\_ETRS}$) to converge to a cumulative dose ($D_{cumulative}$) that meets the one or more cost functions. In some variations, methods for joint optimization may comprise calculating the radiation dose ($D_{0\_ITRS}$) deliverable using the ITRS by calculating a ITRS dose-mapping matrix (R) that maps a radiation dose to a plurality of patient regions resulting from applying a quantity of ITRS (q) to the patient, where $D_{0\_ITRS}=Rq$, calculating the radiation dose ($D_{0\_ETRS}$) deliverable using the ETRS by calculating a ETRS dose-mapping matrix (A) that maps a radiation dose to a plurality of patient regions resulting from applying a radiation fluence (x) to the patient, where $D_{0\_ETRS}=Ax$, and $D_{cumulative}=Ax+Rq$, and adjusting the radiation dose ($D_{0\_ITRS}$) deliverable using the ITRS and/or the radiation dose ($D_{0\_ETRS}$) deliverable using the ETRS by solving for x and q such that one or more cost functions are met for $D_{cumulative}=Ax+Rq$. The one or more cost functions may comprise a cost function C(x) on radiation fluence (x), and/or a cost function C(q) on ITRS quantity (q), and/or a cost function C(Ax) on $D_{0\_ETRS}$, and/or a cost function C(Rq) on $D_{0\_ITRS}$, and/or a cost function $C(D_{cumulative})$. For example, the one or more cost functions may comprise a cumulative cost function with a weighting factor for each cost function.

$$C=\Sigma w_i C_i(x)+\Sigma w_j C_j(q)+\Sigma w_k C_k(Ax)+\Sigma w_l C_l(Rq)+\Sigma w_m C_m(D_{cumulative})$$

Any one of the one or more cost functions may comprise a cost function on radiation toxicity to a non-target region. The weighting factor for each cost function may represent a priority ranking of that cost function relative to other cost functions. For example, at least one weighting factor for a cost function may be assigned the highest priority ranking and may have the highest weighting factor, and the cost functions with lower priority rankings may each have a range of acceptable weighting factors that may be lower than the highest weighting factor.

In some variations, adjusting the radiation dose the radiation dose ($D_{0\_ITRS}$) deliverable using the ITRS and/or the radiation dose ($D_{0\_ETRS}$) deliverable using the ETRS may comprise adjusting the ETRS radiation dose ($D_{0\_ETRS}$) based on the ITRS radiation dose ($D_{0\_ITRS}$). Adjusting the radiation dose the radiation dose ($D_{0\_ITRS}$) deliverable using the ITRS and/or the radiation dose ($D_{0\_ETRS}$) deliverable using the ETRS may comprise adjusting the ITRS radiation dose ($D_{0\_ITRS}$) based on the ETRS radiation dose ($D_{0\_ETRS}$). The radiotherapy treatment plan may further specify a first number of treatment sessions using the ITRS and a second number of treatment sessions using the ETRS. The ITRS may comprise an injectable compound with a targeting backbone and a radionuclide, and the radiotherapy treatment plan may further specify a volume of the injectable compound to be injected at each of the first number of treatment sessions. Alternatively, or additionally, the ITRS may comprise an implantable radiation source comprising a radioactive portion and a housing disposed over the radioactive portion, and the radiotherapy treatment plan may further specify a radioactivity level of the radioactive portion. The implantable radiation source may comprise a radioactive seed, and the radiotherapy treatment plan may further specify a number of seeds to be implanted and the location of the seeds at the patient target region. Alternatively, or additionally, an implantable radiation source may comprise radioactive tubes or wires, and the radiotherapy treatment plan may further specify the implantation location of the tubes or wires, the number of tubes or wires, the implantation time, and/or the radioactivity levels of the tubes or wires. In some variations, the radiation dose to be delivered using the ETRS ($D_{ETRS}$) may be represented by a delivery fluence map. For example, the method may comprise generating instructions for the external therapeutic radiation source and a multi-leaf collimator of the external therapeutic radiation source based on the delivery fluence map, where the instructions for the external therapeutic radiation source comprise one or more radiation emission positions and the instructions for the multi-leaf collimator comprise one or more leaf configurations that correspond with the one or more radiation emission positions. The radiotherapy plan may comprise one or more firing filters for each radiation emission position of the ETRS, where the one or more firing filters may be shift-invariant and may represents a mapping between the delivery fluence map and an image that includes the patient target region.

The radiation dose to be delivered using the ITRS ($D_{ITRS}$) may be represented by dose per volume of the ITRS, and the radiation dose to be delivered using the ETRS ($D_{ETRS}$) may be represented by a delivery fluence map. Alternatively, or additionally, the radiation dose to be delivered using the ITRS ($D_{ITRS}$) may be represented by dose per volume of the ITRS, and the radiotherapy plan may comprise a series of ETRS machine instructions for delivering the ETRS radiation dose ($D_{ETRS}$). The cumulative radiation dose ($D_{cumulative}$) may include a dose uncertainty that is represented by a bounded dose-volume histogram (bDVH) having an upper bound curve and a lower bound curve, and adjusting the radiation dose ($D_{0\_ITRS}$) and/or the radiation dose ($D_{0\_ETRS}$) may comprise changing the radiation dose ($D_{0\_ITRS}$) and/or the radiation dose ($D_{0\_ETRS}$) such that the sum of $D_{0\_ITRS}$ and $D_{0\_ETRS}$ results in a nominal dose curve that is within the upper bound curve and lower bound curve of the cumulative radiation dose ($D_{cumulative}$) bDVH.

Disclosed herein are methods for joint internal and external radiotherapy. One method for joint radiotherapy may comprise generating a radiotherapy treatment plan that specifies a radiation dose ($D_{ITRS}$) deliverable using an internal therapeutic radiation source (ITRS) and a radiation dose ($D_{ETRS}$) deliverable using an external therapeutic radiation source (ETRS), where the radiation doses ($D_{ITRS}$) and ($D_{ETRS}$) have been calculated by iterating through intermediate values of ITRS radiation doses and intermediate values of ETRS radiation doses to attain a cumulative radiation dose ($D_{cumulative}=D_{ITRS}+D_{ETRS}$) that meets prescribed dose requirements, delivering radiation in a first treatment session to a patient target region using a radiotherapy system comprising an ETRS movable about a patient target region, and delivering radiation in a second treatment session using an ITRS to the patient target region. Generating the radiotherapy treatment plan may comprise calculating an intermediate value of the ITRS dose ($D_{ITRS}$) using functional image data. Functional image data may comprise PET data, and/or CT data, and/or SPECT data. The ITRS may comprise an injectable compound and calculating an intermediate value of the ITRS dose ($D_{ITRS}$) may use biodistribution data derived from the functional image data. The cumulative radiation dose ($D_{cumulative}$) may meet one or more dose constraints, for example, one or more cost functions. The one or more cost functions may comprise a cost function on radiation toxicity to a non-target region, and/or the one or more cost functions may comprise a cost function on the ITRS dose ($D_{ITRS}$) and/or ETRS dose ($D_{ETRS}$). Delivering radiation in the second treatment session may comprise injecting the ITRS into the patient, where the ITRS comprises a compound with a targeting backbone and a radionuclide. For example, the targeting backbone may be DOTA-TATE and the radionuclide may be selected from a group consisting of Ga-68 and Lu-177. In some variations, the targeting backbone may be selected from the group of consisting of DOTA-TOC, PSMA-11, PSMA-617, NeoBOMB1, Pentixafor, iobenguane (MIBG), TCMC trastuzumab, MDP, iodine, ibritumomab tiuxetan, SAR-TATE, thymidine, methionine, misonidazole (MISO), azomycin-arabinoside, erythronitroimidazole, a nitromidazole derivative, folic acid, 5F7 antibody, choline, DCFPyL, DCFBC, PD-1 binding protein, PD-L1 binding protein, PD-L2 binding protein, satoreotide tetraxetan, lexidronam, tositumomab, apamistamab, lilotomab satetraxetan, omburtamab, 3BP-227, fibroblast activation protein (FAP) inhibitor, FAP binding molecule, girentuximab and pentixather, and the radionuclide may be selected from the group consisting of Ga-68 or Lu-177. In some variations, delivering radiation in the second treatment session may comprise implanting the ITRS at the patient target region, where the ITRS may comprise a radioactive portion and a housing disposed over the radioactive portion. For example, the implantable radiation source may comprise a radioactive seed.

The radiotherapy system further comprises a multi-leaf collimator disposed in a radiation beam path of the ETRS and a movable gantry upon which the ETRS is mounted, and delivering radiation in the first treatment session may comprise moving the gantry to position the ETRS at radiation emission locations and arranging leaves of the multi-leaf collimator at each of the radiation emission locations in order to deliver the ETRS radiation dose ($D_{ETRS}$). The radiotherapy system may further comprise a plurality of PET detectors and delivering radiation in the first treatment session may comprise arranging leaves of the multi-leave collimator and emitting radiation from the ETRS in response to PET detector data.

In some variations, a method for joint internal and external radiotherapy may further comprise acquiring functional image data after delivering radiation using the ITRS, acquiring functional image data after delivering radiation using the ITRS, and delivering the updated ITRS radiation dose ($D_{updated\_ITRS}$) using the ITRS in a third treatment session. Calculating the updated ITRS radiation dose ($D_{updated\_ITRS}$) may comprise calculating a radiation dose delivered in the second treatment session based on the functional image data. For example, calculating the updated ITRS radiation dose ($D_{updated\_ITRS}$) may further comprise calculating a radiation dose delivered in the first treatment session and optionally, calculating a radiation dose delivered in the first treatment session may use the functional image data. Some methods may optionally comprise calculating an updated ETRS radiation dose ($D_{updated\_ETRS}$), and where calculating the updated ITRS radiation dose ($D_{updated\_ITRS}$) and the updated ETRS radiation dose ($D_{updated\_ETRS}$) comprises calculating an updated cumulative dose ($D_{updated\_cumulative}$) by subtracting the radiation doses delivered in the first and second treatment sessions, and iterating through intermediate values of ITRS radiation doses and intermediate values of ETRS radiation doses to attain the updated cumulative radiation dose ($D_{updated\_cumulative}=D_{updated\_ITRS}+D_{updated\_ETRS}$). Acquiring functional image data may comprise acquiring one or more PET image data, CT image data, MRI image data, and/or SPECT image data. In some variations, generating a radiotherapy treatment plan may comprise acquiring functional image data using a first compound having a first targeting backbone and a first radionuclide, and iterating through intermediate values of ITRS radiation doses and intermediate values of ETRS radiation doses that have been calculated based on the acquired functional image data. Delivering radiation in the second treatment session may use an ITRS that comprises a second compound having a second targeting backbone and a second radionuclide. In some variations, the first targeting backbone and the second targeting backbone are the same, and/or the first radionuclide and the second radionuclide are the same. Acquiring functional image data may comprise acquiring one or more PET image data, CT image data, MRI image data, and/or SPECT image data.

In some variations, the functional image data may be acquired using a first compound comprising a first targeting backbone and a first radionuclide, and the ITRS may be a second compound comprising a second targeting backbone and a second radionuclide. The first targeting backbone and the second targeting backbone may be the same, and/or the first radionuclide and the second radionuclide are the same. The functional image data may be acquired during a diagnostic imaging session, and/or the functional image data may be acquired during a previous treatment session using an ETRS of a radiotherapy system. In some variations, the functional image data may be acquired using an imager of the radiotherapy system.

BRIEF DESCRIPTION OF THE DRAWINGS

FIG. 2A depicts the IRT dose ($D_{irt}$) distribution and DVH curves, FIG. 2B depicts the EBRT dose ($D_{ebrt}$) distribution and DVH curves, and FIG. 2C depicts the combined IRT and EBRT dose ($k_iD_{irt}+k_eD_{ebrt}$) distribution and DVH curves resulting from a simulation of a combined external and internal radiotherapy dose delivery without joint optimization.

FIG. 5C depicts the IRT dose ($D_{irt}$) distribution and DVH curves, FIG. 5D depicts the EBRT dose ($D_{ebrt}$) distribution and DVH curves, and FIG. 5E depicts the combined IRT and EBRT dose ($k_iD_{irt}+k_eD_{ebrt}$) distribution and DVH curves resulting from a simulation of a combined external and internal radiotherapy dose delivery with joint optimization.

FIG. 8 depicts a table that summarizes several examples of radiopharmaceutical compounds that may be used for image data acquisition (e.g., functional image data) and radiotherapy.

FIG. 11 depicts another variation of a radiotherapy system.

DETAILED DESCRIPTION

Disclosed herein are systems and methods for generating a joint radiotherapy treatment plan by jointly optimizing for both the radiation dose provided by an internal therapeutic radiation source (ITRS) and the radiation dose provided by an external therapeutic radiation source (ETRS). One variation of a method comprises jointly optimizing both the radiation dose or fluence deliverable by an external beam radiation therapy (EBRT) system and the injected radiation dose of a radionuclide (e.g., IRT). In some variations, the joint optimization of radiation deliverable by both internal therapeutic radiation source(s) and external therapeutic radiation sources may be done only once before start of a treatment period. A treatment period may comprise multiple treatment sessions, some of which may be ITRS treatment sessions and some of which may be ETRS treatment sessions. Optionally, after one or more ETRS and/or ITRS treatment sessions in a treatment period, the ITRS and ETRS radiation dose may be jointly re-optimized based on updated or newly-acquired image data, such as image data (e.g., functional image data) acquired during or between a treatment session. Jointly optimizing the ITRS and ETRS radiation dose between treatment sessions and/or throughout the course of a treatment period may help to adapt the radiation therapy to account for biological changes in the patient.

Figure 1:
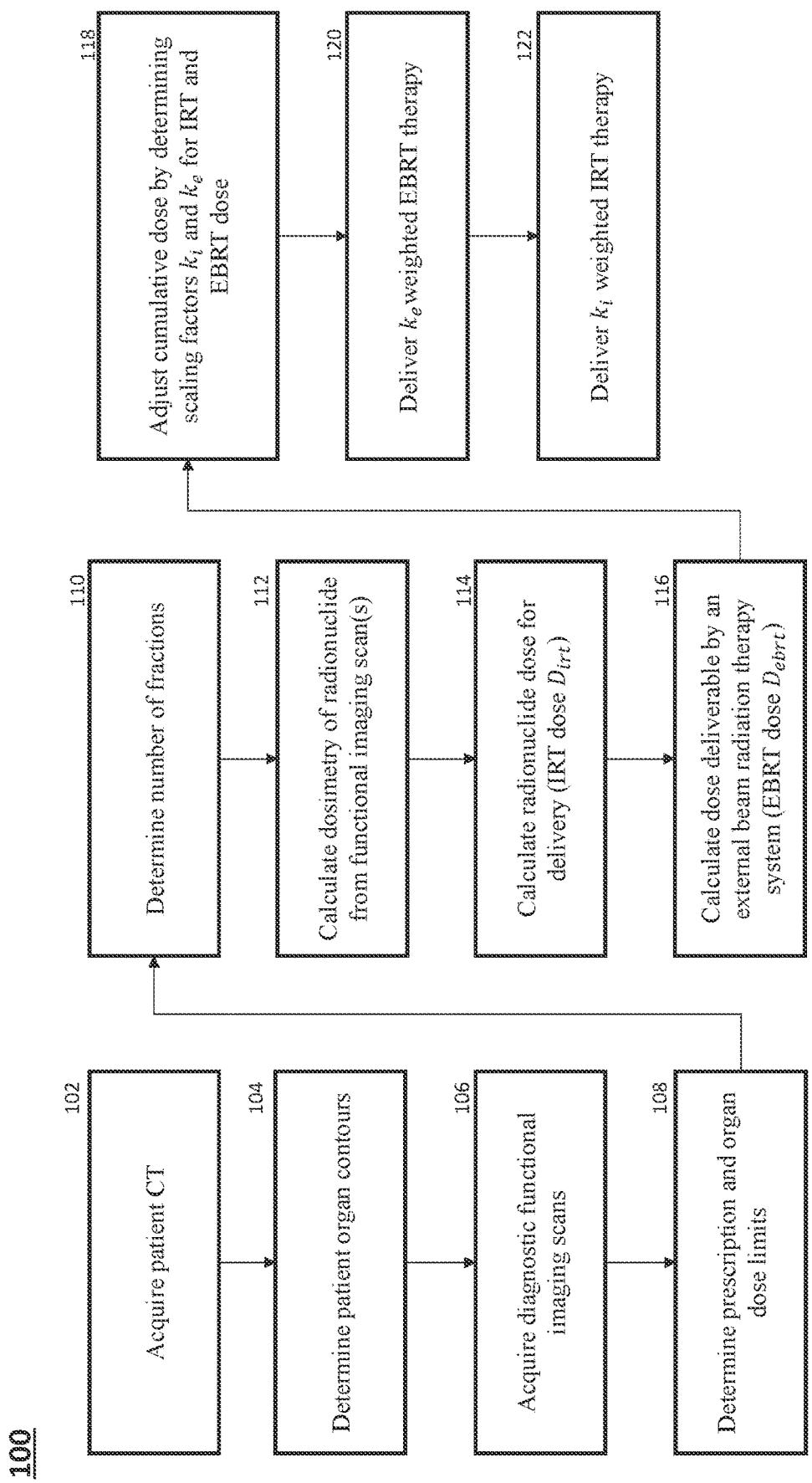
FIG. 1 depicts a flowchart representation of a method for delivering external and internal radiotherapy without joint optimization.

Generating a radiotherapy treatment plan by jointly optimizing for ITRS dose and ETRS dose may result in a cumulative dose profile that has better dose homogeneity in patient target regions than generating a radiotherapy treatment plan by separately optimizing ITRS and ETRS doses. Radiotherapy treatment plans that separately optimize ITRS and ETRS dose usually involve calculating an EBRT treatment plan using traditional radiotherapy treatment planning methods, and separately calculating the IRT dose. While calculating the EBRT treatment plan, the IRT dose is either not considered at all or simply treated as a fixed dose quantity. Similarly, while calculating the IRT dose, the dose provided by an external therapeutic radiation source is not considered. Before treatment, the separately calculated EBRT treatment plan and IRT dose may be combined, and may each be multiplied by a scaling factor in order to obtain a cumulative dose that meets prescribed dose levels and constraints. FIG. 1 depicts one example of a method (100) for generating a combined radiotherapy treatment plan that separately optimizes ITRS dose and ETRS dose (i.e., does not jointly optimize ITRS and ETRS dose), and delivers a combined dose that is a sum of ITRS dose and ETRS dose, each optionally multiplied by a scaling factor. Method (100) may comprise acquiring (102) patient anatomical data (e.g., CT image data), determining (104) patient organ contour data, acquiring (106) diagnostic functional imaging scans and/or functional image data, determining (108) prescription dose and organ dose limits and constraints, and determining (110) the number of fractions or treatment sessions in a treatment period. After these treatment parameters (e.g., prescribed dose to patient target regions, dose limits to organs at risk or OARs, dose constraints, number of fractions, etc.) have been determined, method (100) may comprise calculating (112) the ITRS or radionuclide dose based on the functional image data and then calculating (114) the radionuclide dose for delivery (IRT dose $D_{irt}$). For example, IRT dose is typically calculated based on patient weight and evaluated for toxicity based on functional image data. Functional image scans comprise image data that represent the biological distribution of a molecule (e.g., an imaging tracer such as a compound having a radionuclide and/or radiopharmaceutical) inside of a patient. In some variations, functional image data may be used to generate an image or map of the biodistribution and/or pharmacokinetics of the molecule within a patient. Functional image data may be combined (e.g., overlaid) with an anatomical image. Examples of functional image scans may include PET scans or SPECT scans, where the functional PET or SPECT image data provides information about the distribution of the PET or SPECT tracer within a patient. These scans may be combined with a CT scan, e.g., PET/CT, SPECT/CT scans. While the various methods disclosed herein are described in the context of using functional image data such as PET image data or SPECT image data, it should be understood that the methods may also use any imaging modalities, such as CT image data, MR image data, ultrasound image data, molecular image data, nuclear image data, etc.

In some variations, the imaging tracers used to generate imaging scans (e.g., functional imaging scans) may comprise a targeting backbone or carrier molecule that binds to specific cellular markers and a radioactive isotope (e.g., a positron-emitting isotope in the case of PET imaging). The targeting backbone may selectively bind to specific tumors, while the radioactive isotope may act as a marker that indicates the location of the tracer. Alternatively, or additionally, the radioactive isotope may act as a therapeutic radiation source that lethally irradiates a tumor when a sufficient quantity of the tracer accumulates at the tumor. A "theranostic" may be a compound that acts as both an imaging agent and a therapeutic agent; that is, having both therapeutic and diagnostic functions. An example of a theranostic compound is lutetium Lu-177 DOTA-TATE (e.g., LUTATHERA®), a labeled somatostatin analogue peptide. As a diagnostic agent, Lu-177 DOTA-TATE emits low energy gamma rays. These gamma rays can be imaged using SPECT or gamma cameras. For example, long term (i.e., over multiple days) pharmacokinetic information of the Lu-177 low-energy gamma-emitting image may be used to estimate the absorbed dose of the theranostic over the treatment period. In some variations, an imaging tracer with a targeting backbone and a radioactive isotope may be used for image scanning, and a radiopharmaceutical compound having the same targeting backbone, but a different radioactive isotope may be used for treatment. The same molecule, Lu-177 DOTA-TATE, also has a PET emitting version, Ga-68 DOTA-TATE. The PET images may have much better contrast, quantification, and resolution than the SPECT or planar gamma camera images of Lu-177. In some variations, the Ga-68 DOTA-TATE may be used for initial diagnostic evaluation to determine whether the patient is a candidate for Lu-177 DOTA-TATE therapy. Over the course of treatment, SPECT or planar gamma camera images of the Lu-177 may be used to monitor the pharmacokinetics during the treatment period. Both the initial Ga-68 DOTA-TATE and the SPECT Lu-177 DOTA-TATE images are images that may be used to determine the absorbed dose of the radiopharmaceutical.

Method (100) may comprise separately calculating (116) a dose deliverable by an external beam radiation therapy system and EBRT dose ($D_{ebrt}$), and then adjusting (118) the cumulative IRT and EBRT dose by calculating the scaling factors $k_i$ and $k_e$ for the IRT dose and EBRT dose, respectively. Calculating the scaling factors $k_i$ and $k_e$ may comprise determining the values of kl and $k_e$ such that the cumulative IRT and EBRT dose ($k_iD_{irt}+k_eD_{ebrt}$) meets the prescribed dose to patient target regions. While adjusting the cumulative dose (118) for delivery, the calculated EBRT dose $D_{ebrt}$ and the calculated IRT dose $D_{irt}$ are not modified. Method (100) may then comprise delivering (120) the EBRT radiation dose ($k_eD_{ebrt}$) to the patient and then delivering (122) the IRT radiation dose ($k_iD_{irt}$) to the patient. Linearly scaling the EBRT radiation dose may comprise modifying the dose rate of the ETRS, i.e., adjusting the number of therapeutic radiation beam pulses emitted per unit time. Linearly scaling the IRT radiation dose may comprise linearly scaling the volume of the radionuclide and/or radiopharmaceutical that is injected or implanted into the patient.

However, linearly scaling and summing the IRT and EBRT radiation doses that have been separately optimized retains the heterogeneous dose distribution that results from IRT. FIGS. 2A-2C depict the dose distribution (upper plots) and dose-volume histogram DVH (lower plots) for a simulation of a treatment planning method that separately optimizes ITRS and ETRS dose, and scales and sums the doses for delivery. The PTV is represented by the outer black line (200) in the top panels of FIGS. 2A-2C. FIG. 2A depicts the IRT dose ($D_{irt}$) distribution and DVH curves, FIG. 2B depicts the EBRT dose ($D_{ebrt}$) distribution and DVH curves, and FIG. 2C depicts the combined IRT and EBRT dose ($k_iD_{irt}+k_eD_{ebrt}$) distribution and DVH curves. The DVH curve (202) corresponds to the dose delivered per volume fraction/proportion of the PTV. FIG. 2A shows that a radionuclide is able to provide a high dose to a relatively small proportion of the PTV (e.g., per the lower plot, the DVH curve shows that less than 10% of the PTV receives a dose greater than about 25 Gy), and that the high-dose region is located at the center of the PTV (e.g., per the upper plot, the high-intensity region is in the central portion of the PTV (200)). FIG. 2B shows that EBRT is able to provide a more homogeneous dose to the PTV (e.g., per the lower plot, the DVH curve shows that 100% of the PTV receives a dose that is greater than about 50 Gy with a steep fall-off), and that the high-dose region encompasses nearly the entirety of the PTV (e.g., per the upper plot, the high-intensity region spans nearly all of the PTV (200)). However, when the IRT and EBRT doses are combined, the cumulative dose distribution in the PTV is relatively heterogeneous. The upper plot of FIG. 2C shows that the high-dose region is still largely located at the center of the PTV, and the DVH curve shows a slower dose fall-off. For example, while 80% of the PTV receives a dose of about 58 Gy, 20% of the PTV receives a dose of about 77 Gy, a dose spread (204) of about 19 Gy over 60% of the PTV. Another way to quantify the effect is called the homogeneity index (HI). HI may be calculated by dividing the maximum dose or intensity level of the PTV by the minimum dose or intensity of the PTV. The HI over the PTV (200) when combining IRT dose and EBRT dose that have been separately optimized is 95 Gy/50 Gy or approximately 1.9. While linearly combining IRT dose and EBRT dose irradiate the majority of a tumor with sufficient levels of radiation, the heterogeneity may miss cancer cells at the edges of the tumor, which may increase the likelihood of recurrence. Furthermore, adjusting the delivered dose by a scaling factor may provide a lethal dose of radiation to the tumor(s), however, may also increase toxicity to the patient and expose the patient to unnecessarily high levels of radiation.

In contrast, a treatment planning method that comprises jointly optimizing the radiation dose from internal therapeutic radiation sources and external therapeutic radiation sources may help provide a therapeutic and more homogeneous dose of radiation to tumor(s) with potentially less toxicity. Combining both ITRS and ETRS radiation therapy and jointly optimizing for the radiation dose provided by both modalities may also facilitate precise treatment of metastatic cancer while minimizing the significant toxicity that can result from either modality. The joint radiotherapy treatment planning methods described herein comprise adjusting both the ITRS radiation dose and the ETRS radiation dose during the optimization step of treatment planning. Adjusting both ITRS and ETRS radiation doses may comprise modifying the ITRS dose distribution in conjunction with the ETRS dose distribution (and/or vice versa) and evaluating the cumulative ITRS and ETRS dose distribution to determine whether dose constraints are met. Jointly optimizing ITRS and ETRS dose together may impose dose constraints on the ITRS dose (and therefore, the combined dose) that are not typically included when ITRS dose is calculated separately. This may provide more granular and precise adjustment of the cumulative dose distribution so that dose and toxicity constraints are met while providing lethal doses of radiation to cancer cells.

Synergy Between Internal Radionuclide Therapy (IRT) and Biologically-Based External Beam Radiation Therapy (EBRT)

Furthermore, EBRT methods that use image data (e.g., functional image data) for radiation delivery may have additional synergies with treatment planning methods that comprise joint optimization of ITRS and ETRS radiation dose. As described above and depicted in the method flowchart in FIG. 1, imaging scans of a patient using a radionuclide may be necessary for calculating the dosimetry of radionuclides and to determine how much (e.g., volume) radionuclide is to be injected in order to deliver a prescribed dose. Most EBRT methods do not require imaging scans, so a joint IRT and EBRT treatment plan would involve an "extra" imaging session. However, the generation of an EBRT treatment plan that relies on image data for radiation delivery already includes an imaging session, so the same image data used for EBRT treatment planning may also be used for IRT treatment planning and joint optimization. In one variation, the imaging agent used in the imaging session may have the same targeting backbone as the radiopharmaceutical used to deliver IRT. One example of an EBRT method that uses imaging data (e.g., functional imaging data) to guide radiation delivery is biologically-guided radiotherapy (BGRT). BGRT guides radiation to a patient based on PET image data acquired during a treatment session. A PET tracer is injected into a patient before the treatment session (e.g., as part of treatment planning and/or at the start of a treatment session), and the rate of PET tracer uptake and/or the location(s) of PET tracer accumulation provide biodistribution and/or pharmacokinetics data that represents the biological state and/or function of a patient's physiology. This data may be used to guide external beam radiotherapy and/or to calculate the dosimetry of a radionuclide. An image scan using a positron-emitting isotope attached to a targeting backbone may be used in the dosimetry calculations of the radiopharmaceutical compound having the same targeting backbone. In this way, BGRT and IRT may use the same PET tracer for diagnostic analysis for dosimetry for IRT and biological guidance for BGRT. For example, a PET imaging tracer may comprise a PET emitting isotope (e.g., Ga-68) attached to the targeted peptide DOTA-TATE and a radiopharmaceutical compound for treatment may have a beta emitting isotope (e.g., Lu-177) attached to the targeted peptide DOTA-TATE. This PET imaging tracer and radiopharmaceutical compound may be paired together for the diagnosis and treatment of somatostatin positive neuroendocrine tumors. Similarly, a single-photon emitting isotope suitable for SPECT imaging may be attached to a targeting backbone for imaging, while a radiopharmaceutical with the same targeting backbone but different radioactive isotope may be used for treatment.

While the examples disclosed herein pertain to joint optimization of radiation doses deliverable using one or more radionuclides and one or more external high-energy photon sources, it should be understood that the methods described herein may be used for joint optimization of radiation doses deliverable using any internal therapeutic radiation source (ITRS) and any external therapeutic radiation source (ETRS). An ITRS may comprise any compound or device that is configured to emit therapeutic levels of radiation from inside a patient's body, for example, a radionuclide (RN), a radiopharmaceutical, and/or a radioactive seed or microsphere (e.g., brachytherapy devices). In some variations, an ITRS may be injectable into the bloodstream of a patient and/or implantable at a patient target region. For example, a radioactive seed or microsphere may be injectable into the patient bloodstream and/or may be implantable at a patient target region. Internal radionuclide therapy (IRT) refers to any radiotherapy method where the therapeutic radiation source comprises a RN (including radionuclides that operate alone or in conjunction with a targeting backbone as part of a radiopharmaceutical) that is injected or implanted or otherwise attached to the patient's body. An "ITRS dose" refers to a radiation dose provided by an internal therapeutic radiation source.

An ETRS may comprise any compound or device that is configured to emit therapeutic levels of radiation from outside a patient's body and can be directed toward patient target regions. For example, an ETRS may comprise a source of high-energy photons (e.g., X-rays or gamma rays) or particles (e.g., protons, neutrons, electrons, etc.), and may include linear accelerators (linacs), a cobalt-60 source, proton beam source, neutron beam source, betatron, and the like. One or more ETRS may be included as part of an external beam radiotherapy (EBRT) system. EBRT involves generating high-energy photon or particle beam and shaping the beam to direct it to target regions while shielding non-target regions. EBRT systems may comprise one or more high-energy photon and/or particle sources and a beam-shaping assembly that may comprise one or more jaws and collimators. Examples of EBRT systems include stereotactic body radiotherapy (SBRT) systems, intensity-modulated radiotherapy (IMRT) systems, image-guided radiotherapy (IGRT) systems, biologically-guided radiotherapy (BGRT) systems, etc. Additional details and examples of EBRT systems are provided below. An "ETRS dose" refers to a radiation dose provided by an external therapeutic radiation source.

Methods for Joint Radiotherapy Treatment Planning

Methods for generating a joint radiotherapy treatment plan that irradiates one or more patient target regions may comprise jointly optimizing the radiation dose and/or fluence to be delivered using one or more ITRS and one or more ETRS. The method may then comprise jointly optimizing an external beam radiotherapy plan in conjunction with the radionuclide dosimetry based on a set of clinician-determined dose constraints. More generally, joint optimization of ITRS and ETRS doses may comprise adjusting both the ITRS radiation dose and the ETRS radiation dose (e.g., dose distributions) iteratively to meet prescribed dose constraints for one or more patient target regions. Dose constraints may be defined (e.g., by a clinician and/or medical physicist) for one or more patient target regions, and the constraints may comprise one or more cost functions. Cost functions may include penalty functions and may include constraints on the toxicity of the ITRS to non-target regions such as healthy tissue and/or organs-at-risk (OAR), as well constraints on the radiation dose delivered by both the ITRS and ETRS. One example of ITRS-specific constraints relates to limiting broad hematological toxicity (e.g., sparing toxicity to the white blood cells by limiting the mean ITRS radiation dose). Other examples of ITRS-specific constraints are on the minimum and maximum of the injected ITRS radiation dose to handle practical constraints on the preparation and injection of the RN or to help ensure that a minimum amount of RN is injected to treat non-visible micro-metastases. For example, injectable RN or radiopharmaceuticals may only be available in certain volumes (e.g., absolute volume in mL, or radioactivity levels per unit volume kBq/mL) or discrete or quantized radiation dose levels (e.g., absolute dose levels in Gy, or dose levels per unit radioactivity Gy/kBq, or radioactivity levels µC). For example, an injectable RN may be provided from about 100 mC to about 300 mC, in increments of about 100 mC. During the joint optimization of the ITRS dose and ETRS dose, the ITRS dose may be constrained to the pre-specified injectable volumes and/or radiation quanta. In joint optimization, both the ITRS dose and the ETRS dose are iteratively adjusted until dose requirements and/or constraints are met. After joint optimization, a joint radiotherapy treatment planning method may comprise calculating a quantity of the ITRS that is to be introduced into the patient to deliver the ITRS dose, and the calculated quantity of ITRS may be injected and/or implanted into the patient. For example, the treatment planning method may comprise calculating a volume of a RN and/or radiopharmaceutical that is to be injected into the patient at each treatment session. Alternatively, or additionally, the treatment planning method may comprise calculating a quantity of radioactive seeds and/or microbeads to be implanted at one or more patient target regions. In some variations, an implantable radiation source may comprise radioactive tubes or wires, and the radiotherapy treatment plan may further specify the implantation location of the tubes or wires, the number of tubes or wires, the implantation time, and/or the radioactivity levels of the tubes or wires. A joint radiotherapy treatment planning method also comprises calculating a delivery fluence map for an EBRT system and/or generating a set of EBRT system machine instructions for each treatment session. A delivery fluence map may comprise a set of beamlets and beamlet intensities for delivery using a high-energy beam during a treatment session. In some variations, an EBRT system may segment the delivery fluence map calculated by the treatment planning method into machine instructions during the treatment session (i.e., real-time segmentation where machine instructions are not calculated before the treatment session). Alternatively, an EBRT system may execute the machine instructions generated by the radiotherapy treatment planning system.

In some variations, generating a radiotherapy treatment plan may comprise acquiring planning images (e.g., CT images, functional image data such as PET image data), defining the contours of the patient target regions, calculating the dosimetry of a RN (or any ITRS), and determining the dose prescription for the patient target regions, OARs, and/or any other region of interest. A dose prescription may include the dose constraints that the ITRS/ETRS combined therapy needs to meet for a desired therapeutic effect. For example, the dose prescription may define the minimum necessary dose a patient target region must receive in order to reduce or block the proliferation of cancer cells. A dose prescription may also define the maximum dose that an organ system may receive to avoid unwanted side effects. In some variations, the course of treatment during a treatment period may be predefined by the clinician. For example, the clinician may determine the number and order of ITRS and ETRS treatment sessions in a treatment period. For example, a ETRS treatment session may be coupled with one ITRS treatment session. Alternatively, or additionally, several ETRS treatment session may precede an ITRS treatment session (or vice versa). The number, order, and type of treatment sessions may be used to calculate the ITRS dose and the ETRS dose so that they may be summed into the same equivalent dose space. The equivalent dose space may be scaled in units relevant for ETRS delivery (Gy), and/or in units relevant for ITRS delivery (absorbed Gy), and/or in an intermediate ETRS/ITRS dose space. In some variations, a mathematical method called biological-equivalent dose (BED) may be used to renormalize delivered ETRS and/or absorbed ITRS dose based on the fractionization and timing of the delivery of the dose. Some methods may comprise jointly optimizing for ITRS dose and ETRS dose in the BED space.

While the variations of joint radiotherapy treatment planning methods provided herein comprising jointly optimizing ITRS radiation dose and/or ETRS radiation dose, it should be understood that in other variations, joint radiotherapy treatment planning methods may comprise jointly optimizing ITRS radiation fluence and/or ETRS radiation fluence. In some variations, joint optimization methods may comprise optimizing for ITRS radiation dose and ETRS radiation fluence. For example, a joint radiotherapy treatment planning method may comprise jointly optimizing for IRT injection dose and EBRT fluence.

Figure 3:
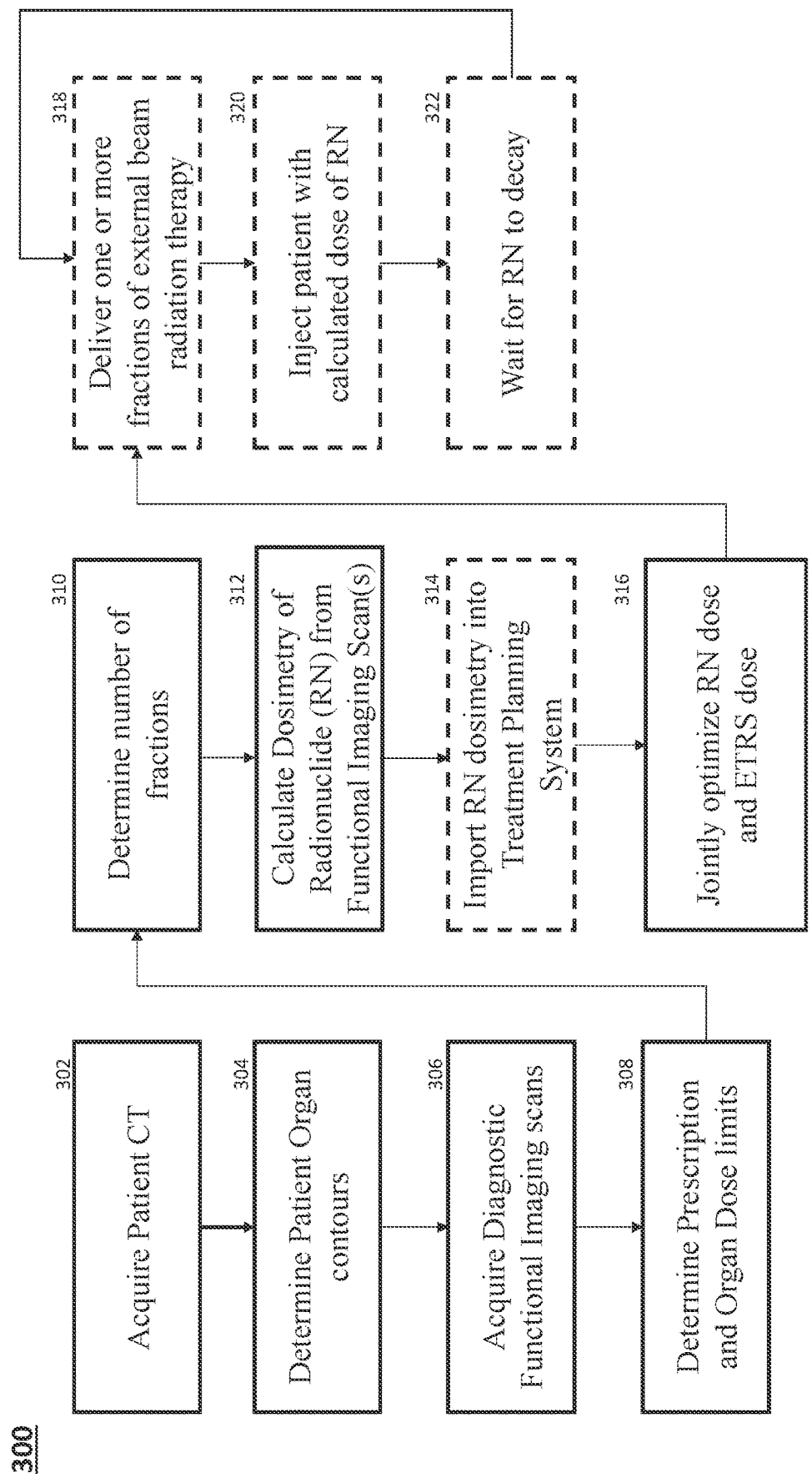
FIG. 3 depicts a flowchart representation of one variation of a method for generating a joint radiotherapy treatment plan that comprises jointly optimizing ITRS and ETRS radiation dose.

FIG. 3 is a flowchart depiction of one variation of a method (300) for generating a joint radiotherapy treatment plan that comprises jointly optimizing ITRS and ETRS radiation dose. Method (300) may comprise acquiring (302) patient anatomical data (e.g., CT image data), determining (304) patient organ contours, acquiring (306) functional imaging scans, determining (308) prescription and organ dose constraints, determining (310) the number of fractions or treatment sessions during a treatment period, and calculating (312) dosimetry of a radionuclide (or any desired ITRS) from the functional imaging scan(s). Optionally, the functional image data, anatomical image data, prescribed dose requirements, and RN dosimetry data may be provided (314) to a treatment planning system, which may comprise software code that may be executed by a treatment planning controller having one or more processors. In some variations, treatment planning analyses and calculations (302-316) of method (300) may be performed directly using the treatment planning system. Method (300) may further comprise jointly optimizing (316) RN dose and ETRS dose to generate a joint radiotherapy treatment plan that specifies a dose to be delivered by the RN and a dose to be delivered using the ETRS (e.g., any EBRT system, BGRT system). In some variations, the joint radiotherapy treatment plan comprises a delivery fluence map and/or machine instructions for an EBRT system and injection volume for a specified type of RN or radiopharmaceutical. The RN dosimetry may be calculated using one or more methods for determining the absorbed dose per unit of injected dose. For example, the RN dosimetry may use the treatment planning CT image for anatomical tissue density data, the functional image of the concentration and/or biodistribution of the radionuclide, a model of the pharmacokinetics over time for the radionuclide, and/or a Monte-Carlo simulation of the of the deposition of energy in the patient. Alternatively, or additionally, the RN dosimetry may be calculated using voxel-based methods based on S-value kernels that compute absorbed dose per unit of injection from an image. Alternatively, or additionally, RN dosimetry may be calculated using convolution of an image using a Dose-Volume-Kernel (DVK). Optionally, RN dosimetry may be further scaled by a biological equivalent dose model, so that the RN dosimetry is in the same scalar space as the ETRS dose.

Determining (310) the number of fractions or treatment sessions in a treatment period may comprise calculating the number of ETRS sessions based on a set number of RN session(s), and/or calculating the number of RN sessions based on a set number of ETRS session(s). The total number of treatment sessions, and/or the number of each type of treatment session (i.e., ETRS session, RN session) may be set by a clinician or a clinic policy, and/or may be calculated by the treatment planning system. The clinician may use clinical trial data to determine the optimal fractionation scheme for a given indication. Additionally, the clinician may use histological or diagnostic blood test information to measure the aggressiveness of the tumor. A more aggressive tumor may have a higher dose per fraction for either ETRS or RN or more fractions to achieve a higher BED dose. Also, the clinician may adjust the fractionization scheme to reduce toxicity to a given OAR. For a treatment planning system to automatically calculate the number of fractions or treatment sessions, a tumor control probability model (TCP) and a normal tissue complication model (NTCP) may be generated for each of the targets and/or the tissues in the patient. The TCP and NTCP models can be used to derive a recommended fractionization scheme to the clinician. Alternatively, the patient may have been treated previously and this information may be used to determine the number of fractions. In some variations, a treatment planning system (i.e., which may also perform the joint optimization methods described herein) may calculate the number of fractions based on the dose prescription in terms of biological effective dose to each patient target region, anatomical location of each patient target region (e.g., "lung, left upper", location data that identifies the relative tumor location and nearby organs-at-risk), pathology data (e.g., tumor staging, whether a patient target region is a primary lesion or a metastatic lesion, genetic test data, and/or histology data), acceptable toxicity risk to organs-at-risk (e.g., normal tissue complication probability NTCP), and/or any prior treatment (e.g., radiation dose, CT/RTSS from prior irradiation, chemotherapy, and/or timing of any prior treatments). A proposed number of treatment sessions or fractions for ITRS and ETRS and a treatment session schedule may be determined and displayed to the clinician on a monitor for selection (e.g., approve and proceed, disapprove and re-calculate) and/or further modification (e.g., approve with clinician modifications).

Method (300) may optionally comprise treating the patient according to the joint radiotherapy plan. For example, method (300) may comprise delivering (318) one or more treatment sessions or fractions using an EBRT system and injecting (320) the patient with the calculated dose of RN in one or more treatment sessions. In some variations, method (300) may optionally comprise waiting (322) for the RN to decay before another EBRT treatment session and/or RN injection (i.e., a RN treatment session). Optionally, between the treatment sessions, additional image data (e.g., functional image data) may be acquired. The additional image data may be used to adapt the EBRT and/or RN dose for a future treatment session. The imaging tracer for the acquisition of image data may have the same targeting backbone as the RN so that the dosimetry of the RN may be updated to reflect any changes in the biological and/or physiological state of the patient as they are being treated (e.g., during the treatment period, between treatment sessions or fractions within the treatment period). In some variations, imaging data acquired during a treatment session and/or images acquired between treatment sessions (e.g., between ITRS treatment sessions, between ETRS treatment sessions, etc.) may be used to adapt the radiation dose for the next treatment session. Adapting a radiation dose for a future treatment session may comprise joint re-optimization with a different number of fractions or treatment sessions for that treatment period (e.g., changing the number of ITRS sessions, the number of ETRS sessions, or both, from the first joint optimization).

Figure 4:
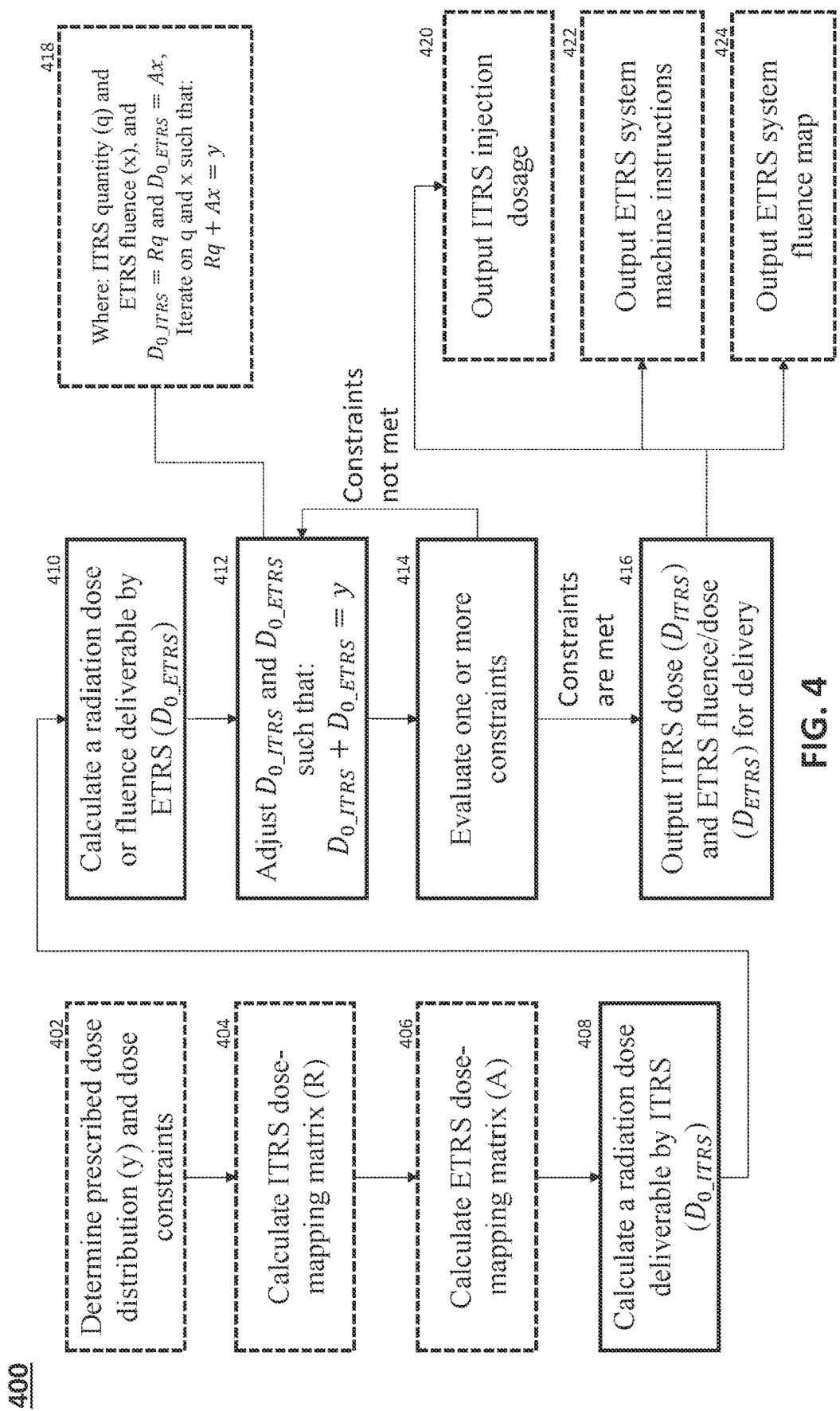
FIG. 4 depicts a flowchart representation of one variation of a method for joint optimization of ITRS radiation dose and ETRS radiation dose.

FIG. 4 depicts one variation of a method for joint optimization of ITRS radiation dose and ETRS radiation dose, which may be used with any of the joint radiotherapy treatment planning methods described herein. Method (400) may comprise calculating (408) a radiation dose that is deliverable by an ITRS ($D_{0\_ITRS}$), calculating (410) a radiation dose that is deliverable by an ETRS ($D_{0\_ETRS}$), adjusting (412) the ITRS and ETRS doses ($D_{0\_ITRS}$, $D_{0\_ETRS}$) to meet the dose prescription (as determined by the clinician), and evaluating (414) one or more prescribed dose requirements (e.g., constraints). If the prescribed dose requirements are not met, method (400) comprises iteratively adjusting the ITRS and ETRS dose distributions ($D_{0\_ITRS}$, $D_{0\_ETRS}$) until the requirements at met. After the dose requirements are met, method (400) may comprise outputting (416) the ITRS dose ($D_{ITRS}$) and ETRS dose ($D_{ETRS}$) for delivery during one or more treatment sessions. In some variations, method (400) may comprise outputting one more of ITRS injection dosage (420), ETRS system machine instructions (422), and/or ETRS system fluence map (424).

In some variations, method (400) may optionally comprise determining (402) the prescribed dose distribution (y) and dose constraints to the patient, calculating (404) an ITRS dose-mapping matrix (R), and calculating (406) an ETRS dose-mapping matrix (A) which may be used to adjust or iterate (412) on the ITRS and ETRS doses ($D_{0\_ITRS}$, $D_{0\_ETRS}$). The prescribed dose distribution may be the cumulative radiation dose to the patient as specified by a clinician and may be represented by a vector of voxels (y) in the patient, each voxel having a dose value. Calculating (404) the ITRS dose-mapping matrix (R) may comprise determining the relationship between the volume of an injected or implanted ITRS and its delivered dose. In some variations, radionuclide dosimetry is performed for a fixed injection volume, and the dosimetry of a radionuclide treatment may be generally linearly related to the amount of radionuclide that is injected. Calculating (404) the ITRS dose-mapping matrix (R) may comprise mapping one or more images (I) (e.g., functional images) to the biologically-equivalent absorbed dose Gy per unit of an injected ITRS (e.g., RN and/or radiopharmaceutical). The images may be acquired using an imaging tracer that has a carrier molecule or targeting backbone that is the same as the carrier molecule or targeting backbone for the ITRS. This mapping (F) may be given by:

$$F\left(I\left[\frac{kBq}{ml}\right]\right) = R\left[\frac{Gy}{kBq}\right]$$

The ITRS radiation dose ($D_{0\_ITRS}$) that is capable of being delivered to the patient may be represented by a similar linear relationship as the injected dose scalar (q, which may, more generally, be a quantity of the ITRS) multiplied by the ITRS dose-mapping matrix (R), which maps the injected dose (q) to the voxelized dosimetry $D_{0\_ITRS}$. That is:

$$D_{0\_ITRS} = Rq$$

Any of the RN dosimetry methods described above may be used to calculate (404) the ITRS dose-mapping matrix (R). Alternatively, or additionally, the ITRS dosimetry may be non-linearly related to the amount of injected ITRS, and may incorporate time-variant pharmacokinetics of the ITRS (e.g., where at high injection volumes, the ITRS has a physiologic effect on the patient that is independent of the ionization radiation).

Alternatively, or additionally to delivering therapeutic doses of radiation using a single radiopharmaceutical in a single treatment session, internal therapeutic radiation may be delivered using multiple different radiopharmaceuticals over one or more treatment sessions. In some variations, an ITRS may comprise two different radiopharmaceuticals. For example, internal therapeutic radiation may be provided by two radiopharmaceuticals that comprise Y-90 and Lu-177. Because the β energy of Y-90 and Lu-177 are different, they may have different dosimetry. By combining the two different radiopharmaceuticals, the ITRS dose distribution may be tuned and adjusted in a way that may not be attainable using a single radiopharmaceutical. The total ITRS dose may be represented by a first injection of a first radionuclide ($q_1$) and a second injection of a second radionuclide ($q_2$). The first and second radiopharmaceuticals may be injected simultaneously or sequentially into the patient. Each radiopharmaceutical may have a different dose mapping matrix ($R_1$, $R_2$), but the doses may sum linearly.

$$D_{0\_ITRS} = R_1 q_1 + R_2 q_2$$

Joint optimization for two radiopharmaceuticals may generate the optimal combination of the two different injected radiopharmaceuticals ($q_1$, $q_2$). For example, one variation of joint radiotherapy treatment may use Lu-177 as a first radionuclide (e.g., Lu-177 conjugated with DOTA-TATE), and Y-90, which has a much larger R range, as a second radionuclide (e.g., Y-90 conjugated with DOTA-TATE). Joint optimization may comprise adjusting the adjusting the injected dose of the two RNs in conjunction with the ETRS dose such that the cumulative dose meets prescribed dose requirements. This method may be extended for any number of N radiopharmaceuticals, e.g., $D_{0\_ITRS} = R_1 q_1 + R_2 q_2 + \ldots + R_N q_N$.

The ETRS dose ($D_{0\_ETRS}$) deliverable to the patient may be modeled as a linear system and calculated by multiplying the ETRS dose-mapping matrix (A) with the ETRS fluence (x) deliverable by a EBRT system (for example) to the patient:

$$D_{0\_ETRS} = Ax$$

Iterating (412-414) on ITRS and ETRS doses may comprise scaling the ITRS and ETRS doses into a dose space that is equivalent to the prescription dose space (418) and iterating on RN quantity (q) and ETRS fluence (x). In some variations, the prescription dose, ITRS dose and ETRS dose may all be defined in the BED space. The sum of ITRS and ETRS doses in the BED space ($D_{cumulative}$) aim to approximate or match the radiation dose prescribed by the clinician, i.e., the prescribed dose distribution (y):

$$D_{cumulative} = y, \text{ where}$$

$$D_{cumulative} = D_{0\_ITRS} + D_{0\_ETRS} = Rq + Ax$$

In addition to requiring that the ITRS and the ETRS radiation dose sum to the prescribed dose distribution, prescribed dose requirements may comprise a set of constraints on all the prescription objectives. In some variations, these constraints may be convex constraints. These convex constraints may imposed on the ETRS fluence (x), on the ITRS quantity (q), on the dose deliverable by the ITRS ($D_{0\_ITRS}$), on the dose deliverable by the ETRS ($D_{0\_ETRS}$), and/or on the cumulative dose ($D_{cumulative} = D_{0\_ITRS} + D_{0\_ETRS}$), and/or on any combination thereof. An example of a convex constraint which may be unique to joint optimization is the minimum dose on the patient target region (e.g., PTV) where $D_{cumulative} = D_{0\_ITRS} + D_{0\_ETRS}$, does not exceed a predefined dose value (in Gy). The ITRS quantity (q) may be constrained to be within a range of acceptable quantities (i.e., q must be within a specified range), and/or may be constrained such that it is an integer multiple of quantized steps. For example, for practical reasons on dosage, the ITRS quantity may be only available in certain discrete dosages. The joint optimization may then have to optimize the injected dose (q) over a limited set of fixed dosages. In some variations, constraints may be derived based on a previously-delivered ITRS dose and/or ETRS dose (e.g., from a previous treatment period, from a previous course of therapy), and/or may optionally include constraints derived from toxicity models of OARs and/or healthy tissue. For example, if an OAR was subject to substantial irradiation in a previous treatment session or period, the dose constraint for the OAR may be more stringent (i.e., to guarantee a lower level of irradiation) for the next treatment session or period. Such toxicity constraints may be applied to the ITRS dose, the ETRS dose, and/or the cumulative dose.

In some variations, these constraints may be weighted by a linear factor that defines or approximates their relative importance. For example, dose constraints may comprise one or more cost functions, and optionally, each cost function may be weighted by an individual scaling factor. Prescribed dose requirements or constraints (C) may comprise one or more cost functions and may include, for example, one or more of a cost function $C(x)$ on radiation fluence (x), and/or a cost function $C(q)$ on ITRS quantity (q), and/or a cost function $C(Ax)$ on $D_{0\_ETRS}$, and/or a cost function $C(Rq)$ on $D_{0\_ITRS}$, and/or a cost function $C(D_{cumulative})$. These may each optionally be weighted by an individual scaling factor ($w_i$, $w_j$, $w_k$, $w_l$, $w_m$). For example, a cost function on the fluence can be used to optimize treatment time in the context of joint delivery. Optionally, a cost function on the ETRS dose may be included to limit skin dose and/or radiation burn toxicity. For example, a cost function on the injected dose (q) can be optimized ensuring that the dose value is one that may be feasible to prepare and introduce into the patient. For example, a cost function of $D_{0\_RN}$ might optimize hematological toxicity (e.g., a cost function that prioritizes the preservation of white blood cells) independent of ETRS dose. Another example is a cost function imposed on the cumulative ITRS and ETRS dose $D_{cumulative}$ that limits the mean combined dose to the heart.

$$C = \Sigma w_i C_i(x) + \Sigma w_j C_j(q) + \Sigma w_k C_k(Ax) + \Sigma w_l C_l(Rq) + \Sigma w_m C_m(D_{cumulative})$$

In some variations, optimization constraints may be met based on a priority ranking. For example, each dose constraint may be ranked, and during optimization, constraints may be satisfied or met based on the corresponding priority ranking. For example, in joint optimization, RN constraints may be prioritized over ETRS constraints or vice versa. Alternatively, for example, the constraints may be prioritized based on organ system so that different ETRS constraints and ITRS constraints may have different priority rankings.

Methods of joint optimization may optionally comprise defining dose constraints where one or more cost functions are designated as high-priority (e.g., mandatory) cost functions, and designating the other cost functions as low-priority (e.g., optional) cost functions. The high-priority cost functions may be assigned the highest possible weight and/or priority ranking, and the low-priority cost functions may be assigned a lower weight and/or priority ranking. In some variations, the high-priority cost functions may have more "stringent" constraints, while the low-priority cost functions may have more "lax" constraints. For example, a high-priority cost function may tightly limit irradiation of the heart (or any desired OAR) to a range that is less than about 1 Gy, while a low-priority cost function may limit irradiation of the tissue around a patient target region to a broader range of no more than about 5 Gy. In some variations, the clinician may prioritize bone marrow toxicity and/or liver toxicity over potential toxicity to the pancreas and/or bladder. That is, the constraints on the bone marrow and/or liver must be met before any constraints on the pancreas and/or bladder are evaluated. In some variations, the clinician may set the weight(s) and/or priority ranking(s) of the high-priority cost functions, and based on this clinician input, the treatment planning system/optimizer may auto-calculate the weight(s) and/or priority ranking(s) of the lower-priority cost functions. During joint optimization, the cumulative RN and/or ETRS dose must satisfy the high-priority cost functions at the specified weight and/or priority ranking (e.g., reduce the value of any high-priority penalty functions), while the low-priority cost functions may be satisfied at varying lower weights and/or priority rankings. For example, the range of acceptable values of low-priority cost functions may be wider than the range of acceptable values of high-priority cost functions. The weights and/or priority rankings of the low-priority penalty functions may be adjusted (e.g., automatically adjusted and/or calculated) relative to each other in order to meet the prescribed dose constraints or requirements. The acceptable ranges may be specified by the clinician and/or calculated by the treatment planning system (and may be subject to clinician review and/or approval).

Some methods of joint optimization may optionally display a set of clinical objectives to a clinician, and the specific dose constraints and cost functions for guiding joint optimization may be defined based on the clinical objectives that are selected by the clinician. This may facilitate the definition of dose constraints and/or setting of specific cost functions for clinicians and reduce the setup time for treatment planning and joint optimization. In addition, defining dose constraints based on clinical objectives may promote ease-of-use and comprehensibility of the treatment planning system for a broader range of clinicians, including but not limited to, radionuclide specialists and radiation oncologists. This may help ensure that the patient's treatment goals and needs are met and help ensure that organs-at-risk are correctly defined for the treatment planning system. In one variation, each clinical objective may be linked to one or more cost functions. In some variations, an example of a clinical objective could be control of all tumors greater than about 1 cm by having a cost function on the minimum dose on the PTV that must be greater than 50 Gy. An example of a clinical objective could be to limit the probability of grade 2 kidney toxicity to less than 10% by linking that to a cost function that limits the maximum kidney dose to less than 40 Gy. Another example of a clinical objective could be to limit the probability of different grades of rectal bleeding as specified by a clinician. For example, a clinician could specify the acceptable risk of rectal bleeding Grade 1 to a first level (e.g., 1.25) or a second level (e.g., 1.10). If the risk of a Grade 1 rectal bleed is set to the first level, the treatment planning system may translate this clinical objective to a dose constraint of V70 Gy≤5% rectal volume; if the risk of a Grade 1 rectal bleed is set to the second level, the treatment planning system may translate this clinical objective to a constraint of V50 Gy≤5% rectal volume. While two levels of clinical risk are provided in this example, it should be understood that there may be any number of clinical risk levels that correspond to a number of cost functions or dose constraints. The cost functions from the one or more clinical objectives may be evaluated during joint optimization. Optionally, when multiple clinical objectives are selected, the clinician may be able to assign a priority or weight to each clinical objective relative to the other clinical objectives (e.g., set a priority ranking for each clinical objective). Joint optimization may then iterate on RN dose and ETRS dose to meet dose constraints and/or cost functions that have been prioritized and/or weighted according to their corresponding clinical objective(s).

In some variations of methods for joint optimization, a convex optimizer may be used to solve for the optimal ETRS fluence (x) and the optimal injected RN dose (q) given dose constraints that comprise one or more of the above cost functions. The optimization may be performed, evaluated, and analyzed in a treatment planning system, and may be reviewed and approved by a clinician.

In some variations, the prescribed dose distribution (y) may be represented by a bounded dose-volume histogram (bDVH) having a nominal prescribed dose curve and any dose delivery uncertainty is represented by an upper bound curve and a lower bound curve. The upper and lower bounds of the prescribed dose distribution bDVH may be calculated based on uncertainties and/or variabilities in radiation dose delivered by an ITRS and/or an ETRS. For example, ETRS dose delivery uncertainties and/or variabilities may arise from patient motion (e.g., respiratory motion, cardiac motion, physiologic motion that may alter the position of the patient target region during radiation delivery), high-energy radiation source precision and/or accuracy, and the like. Since the dose provided by an ITRS is calculated using an imaging scan (e.g., a functional imaging scan), any image base variance in the scan may cause variance in the dose estimate. Imaging scan uncertainties and/or variabilities may arise from variations in blood flow rate, perfusion distribution, pharmacokinetics, binding specificity of the targeting backbone, injection dose measurement, mis-calibration of the scanner, limitations of the image reconstruction algorithm, and the like. ITRS dose delivery uncertainties and/or variabilities may arise from variations in blood flow rate, perfusion distribution, pharmacokinetics, binding specificity of the targeting backbone, injection dose measurement uncertainty, BED modelling errors, and the like. Other ITRS dose variabilities may arise from changes in the patient's physiological or biological state. For example, there may be changes in the patient's metabolism and/or gastrointestinal state (e.g., constipation, gastritis, etc.) that may alter the rate and manner in which an injected or ingested RN or radiopharmaceutical is excreted. If a patient is having gastric issues, a greater percentage of a RN may be excreted through the urinary tract instead of the gastrointestinal tract. There may also be interactions between other medications taken by the patient and the RN or radiopharmaceutical that may affect the ITRS dose and kinetics. ETRS and ITRS dose uncertainties may be combined to derive the upper bound of delivered dose and the lower bound of delivered dose. In some examples, the upper and lower bounds may be derived using models of ETRS and/or ITRS dose uncertainties so that interactions between different uncertainties may be represented in the boundaries of bDVH. Iterating (412-414, 418) on ITRS and ETRS doses in the BED space may comprise adjusting one or both of the $D_{0\_ITRS}$ and $D_{0\_ETRS}$ such that the DVH of the cumulative dose ($D_{cumulative}$) is within the upper and lower bounds of the prescribed dose distribution (y) bDVH. In some variations, this may comprise iterating on RN quantity (q) and/or ETRS fluence (x) until the DVH of the cumulative dose ($D_{cumulative}$) is within the upper and lower bounds of the prescribed dose distribution (y) bDVH. The output or result of jointly optimizing ITRS and ETRS doses may comprise one or more DVH curves that represent one or more cumulative doses (i.e., a range of cumulative doses) that are within the upper and lower bounds of the prescribed dose distribution (y) bDVH. The output of jointly optimizing ITRS and ETRS doses may comprise one or more solutions to the same optimization problem set with different local minima for non-target volumes. For example, if there are three cost functions participating at low cost for different OARs in the optimization that would achieve the target prescription dose equally well, the optimizer may produce DVH curves and dose distributions for each of these results for the clinician to choose between. In all three cases, the prescription dose is met equally well, but the individual doses for OARs may differ substantially. In some variations, the joint optimization may generate a set of DVH curves for the optimized cumulative doses that fall within the upper and lower bounds of the prescribed dose distribution bDVH. Evaluating (414) the constraints may optionally include clinician evaluation and/or selection of a particular dose distribution based on the DVH curves. For example, this set of DVH curves may be displayed to the clinician, along with the individual ITRS dose and the ETRS dose for each of the DVH curves, and the clinician may select one of the DVH curves and its corresponding ITRS and ETRS doses for delivery. For example, in a set of DVH curves that meet the prescribed dose requirements and/or fall within the bounds of the prescribed dose bDVH for a patient target region, the dose to one or more OARs may vary, and as part of evaluating the jointly optimized dose distributions, a clinician may select the dose distribution that delivers less radiation dose to a particular OAR as compared to other dose distributions. After evaluation of the possible radiation doses for delivery based on dose constraints/requirements and/or clinician selection, the joint optimizer may output (416) the ITRS dose and the ETRS fluence/dose that is to be delivered during a treatment period.

After clinician approval of the joint radiotherapy treatment plan, the treatment can be delivered and administered to the patient. In one variation, joint radiotherapy treatment planning only occurs once and the entire course of treatment (i.e., all of the ITRS dose and ETRS dose that were part of the same joint optimization) is delivered to the patient over multiple treatment sessions during a treatment period.

Figure 5B:
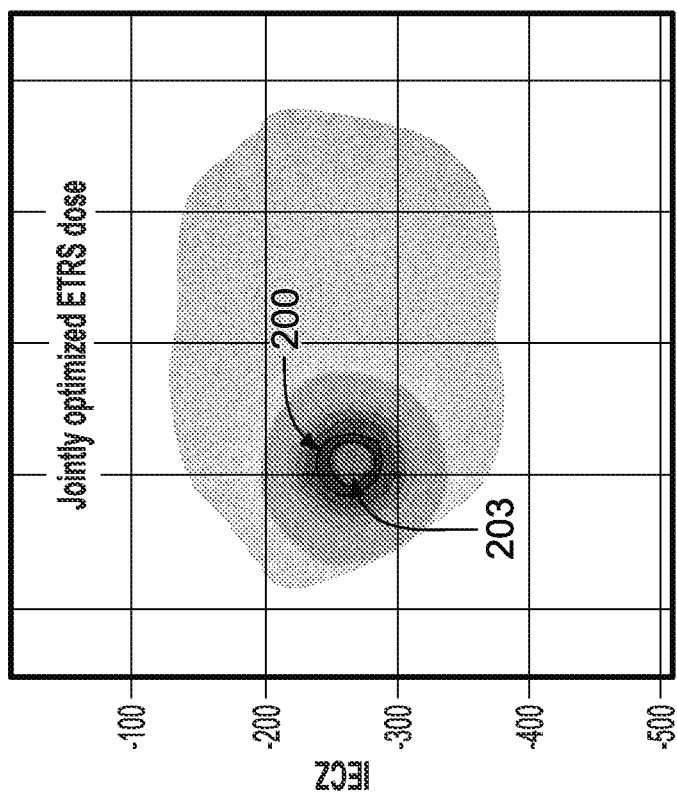
FIG. 5B depicts a simulation plot of ETRS radiation dose distribution that has been jointly optimized with ITRS dose accordingly to the methods described herein.
Figure 5A:
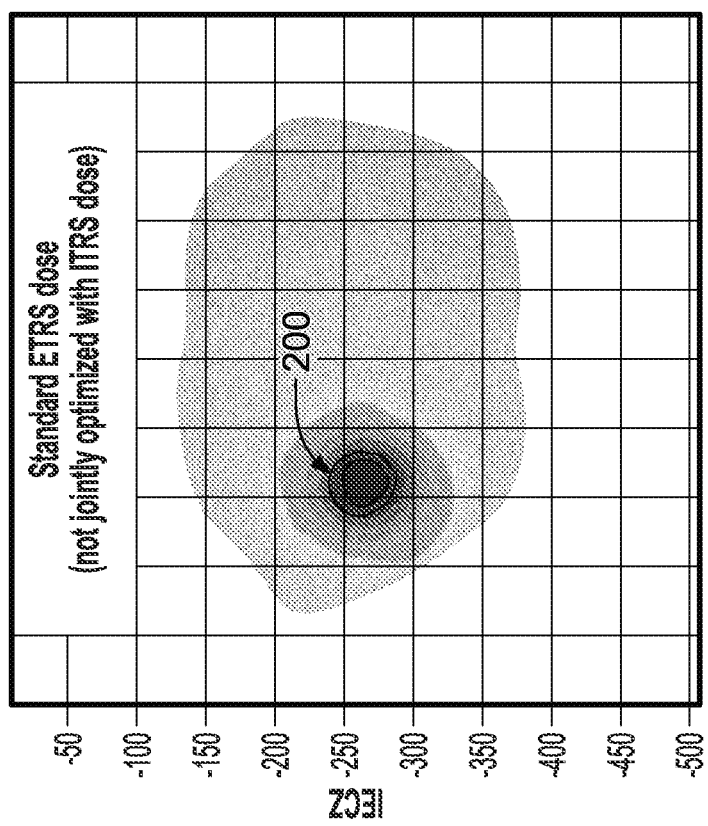
FIG. 5A depicts a simulation plot of ETRS radiation dose distribution that has not been jointly optimized with ITRS dose.

FIGS. 5A-5E depict the ITRS and/or ETRS depict dose distributions ($D_{ITRS}$, $D_{ETRS}$) for a simulation of a treatment planning method that jointly optimizes ITRS dose and ETRS dose using the methods depicted in FIGS. 3-4 and described above. These plots depict the differences in dose distribution when ITRS and ETRS dose are separately optimized as compared to when they are jointly optimized. FIG. 5A depicts an ETRS dose distribution resulting from separately optimizing ETRS dose from ITRS dose (i.e., standard EBRT optimization methods), and FIG. 5B depicts an ETRS dose distribution resulting from jointly optimizing ETRS and ITRS doses (i.e., using the joint optimization methods disclosed herein). As shown in FIGS. 5A-5B, the ETRS dose map has a significantly different dose distribution. The contour of the PTV is represented by the outer black line (200). When ITRS and ETRS doses are not jointly optimized, the ETRS dose distribution is homogeneous over the entire PTV region (FIG. 5A). However, the ETRS dose distribution resulting from joint optimization has a central region of lower dose (203). This "donut" shaped ETRS dose map shown in FIG. 5B reflects the incorporation of ITRS dose to the cumulative dose distribution as part of joint optimization, since ITRS dose tends to aggregate strongly toward the central region of larger tumors. Without jointly optimizing ETRS dose with ITRS dose, the resulting cumulative dose map may create an intense radiation "hot spot" in the center of the PTV. By incorporating the ITRS dose with ETRS dose optimization, the ETRS dose may be reduced for areas in which the ITRS provides a therapeutic level of radiation. This may help reduce the overall radiation exposure and toxicity to the patient, while still providing therapeutic levels of radiation to patient target regions.

FIGS. 5C-5E depict the dose distribution (upper plot) and dose-volume histogram DVH (lower plot) for a simulation of a treatment planning method that jointly optimizes ITRS and ETRS dose. The PTV is represented by the outer black line (200) in the top panels of FIGS. 5C-5E. FIG. 5C depicts the jointly optimized ITRS dose ($D_{ITRS}$=Rq) distribution and DVH curves, FIG. 5D depicts the jointly optimized ETRS dose ($D_{ETRS}$=Ax) distribution and DVH curves, and FIG. 5E depicts the combined jointly optimized ITRS and ETRS dose (Rq+Ax=y) distribution and DVH curves. The DVH curve (212) corresponds to the dose delivered per volume fraction/proportion of the PTV (e.g., a patient target region). FIG. 5C shows that an ITRS such as a RN or radiopharmaceutical compound is able to provide a high dose to a center portion of the PTV (e.g., per the upper plot, the high-intensity region is in the central portion of the PTV (200)). FIG. 5D shows that with joint optimization, the ETRS dose distribution accounts for the contribution of the ITRS (i.e., in the center of the PTV) so that the ETRS dose toward the center portion of the PTV may be reduced, resulting in a "donut" ETRS dose distribution (203). FIG. 5E shows that when the jointly optimized ITRS and ETRS dose distributions are combined, the cumulative dose distribution in the PTV is more homogeneous than when the ITRS and ETRS dose distributions are separately optimized (i.e., in comparison to the dose distributions depicted in FIG. 2C). In particular, the DVH curve for the combined dose distribution in FIG. 5E shows a rapid dose fall-off. For example, 80% of the PTV receives a dose of about 52 Gy and 20% of the PTV receives a dose of about 57 Gy, a dose spread (214) of about 5 Gy over 60% of the PTV (as compared to a dose spread of about 19 Gy in FIG. 2C). The dose distribution may also be quantified as the homogeneity index (HI). An HI that approaches 1 is more homogenous and may be desired because it does not deliver extra dose to the center of the PTV, which may be unnecessary to kill the tumor. In FIG. 5E, the HI of the dose delivered to the PTV by jointly optimizing ITRS dose and ETRS dose is approximately 65 Gy (max)/50 Gy (min) or HI of 1.3. In contrast, as depicted in FIG. 2C, the HI of the dose delivered to the PTV by separately optimizing ITRS dose and ETRS dose is approximately 95 Gy/50 Gy or 1.9. If other higher weight or priority constraints have been met, a jointly optimized plan may have a lower HI value. Jointly optimizing ITRS dose and ETRS dose using the methods disclosed herein may provide a prescribed or desired dose level to patient target regions while reducing excess radiation exposure and/or toxicity to the patient.

Methods for Adapting Radionuclide Dose During a Treatment Period

In some variations, after the ITRS radiation dose and ETRS radiation dose have been jointly optimized, the same ITRS dose may be delivered during each ITRS treatment session or fraction in a treatment period. For example, after RN dose and EBRT dose joint optimization, the volume of RN injected during a RN treatment session may be constant for all of the RN treatment sessions in a treatment period (where a treatment period comprises one or more RN treatment sessions and one or more EBRT sessions). Alternatively, or additionally, the ITRS dose delivered at each treatment session may vary, and in some variations, may be adapted based on updated patient data. Since a radiotherapy treatment period can span over multiple days and weeks, a patient's disease condition and other biological functions may change and be different from the time when the treatment plan was first generated. For example, after an IRT or EBRT treatment session, a new set of images (e.g., functional images) may be acquired, and additional or updated contours of patient target regions and/or organs may be included in the treatment plan. Imaging scans acquired between treatment sessions may point to potential toxicities that were not visible or detectable on the pre-treatment images that were used to generate the initial treatment plan.

In some variations of treatment planning and delivery methods, the radiation dose delivered at each treatment session may be adapted to reflect any biological changes to the patient. One or more of the joint radiotherapy methods described herein may optionally comprise adapting or adjusting the ITRS radiation dose for a future treatment session based on additional image data (e.g., functional image data). Additional image data used to adapt the ITRS radiation dose may be acquired after the treatment planning images, and may include, for example, image data acquired after the treatment plan has been generated, and/or image data acquired during a treatment session. Additionally, or alternatively, the ETRS radiation dose for a future treatment session may be adapted based on additional image data. In some variations, adapting the ITRS dose for a future treatment session may comprise jointly optimizing the ITRS and ETRS radiation dose, as previously described. In this second joint optimization (i.e., joint re-optimization), the radiation dose that has already been delivered in past treatment sessions (from both ITRS and ETRS) may be incorporated such that it is not delivered again. For example, the previously-delivered radiation dose may be converted into the BED space, and may be subtracted from the overall prescribed dose, and the joint re-optimization may proceed based on the remaining (i.e., undelivered) prescribed dose. Alternatively, or additionally, the previously-delivered radiation dose may be used to re-scale the prescribed dose for joint re-optimization. The updated and/or additional image data may be analyzed to determine whether toxicity levels from the RN and/or EBRT are within prescribed tolerance ranges and adjust the future RN and/or EBRT doses accordingly. For example, if image data analysis indicates that toxicity from RN injections is exceeding specified tolerance ranges for one or more patient regions, toxicity constraints (e.g., cost functions, penalty functions) may be adjusted for the re-optimization, e.g., the constraints may be tightened. This may result in, for example, reducing the RN dose for future sessions and increasing the EBRT dose for future treatment sessions to compensate for patient target regions that would have been irradiated with the RN (i.e., EBRT delivery fluence map adapted to have increased fluence levels at areas previously irradiated by a RN).

Image data (e.g., functional image data) may also indicate whether certain sub-regions of a lesion are responding to treatment while other regions of the lesion are not. The ITRS and ETRS dose for future treatment sessions may be jointly re-optimized to direct more ETRS dose to non-responsive patient regions. In some variations, future treatment sessions may increase the ITRS dose to non-responsive patient regions by selecting an ITRS with a different radionuclide (e.g., with higher photon energies) and/or targeting backbone (e.g., that may be more specific and/or have a higher affinity for the non-responsive target regions). Alternatively, or additionally, a clinician may decide to use other treatment methods (e.g., immunotherapy, chemotherapy, etc.) to address the non-responsive patient regions, and as such, the dose for future treatment plans may be jointly re-optimized to reduce or eliminate dose from one or both of ETRS and ITRS to the non-responsive patient regions. In some variations, the dose for future treatment sessions may be adapted and re-optimized using a different ITRS from the previous treatment sessions. Alternatively, or additionally, the adaptation and re-optimization may comprise adjusting the number of ITRS treatment sessions and/or ETRS treatment sessions.

Figure 6:
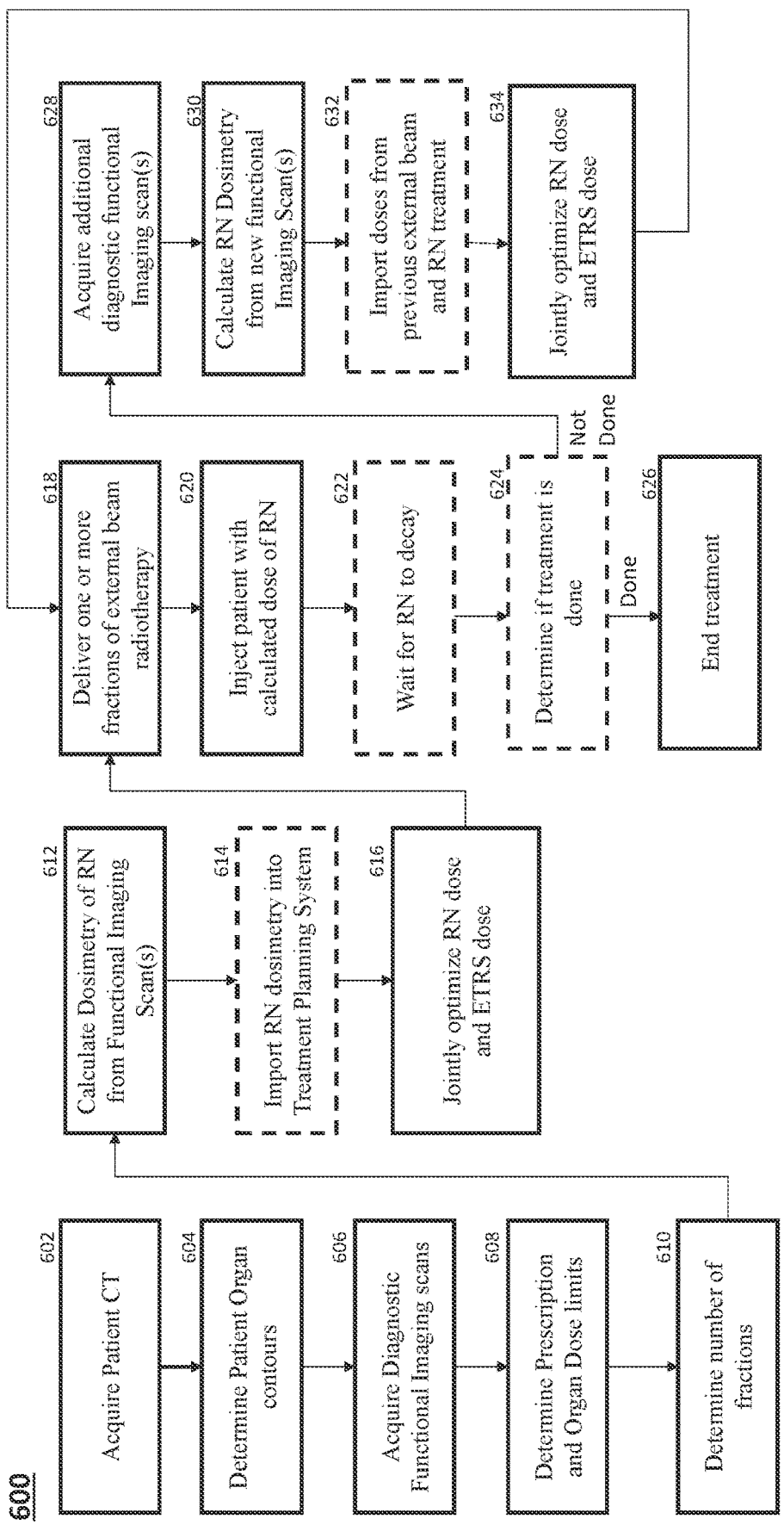
FIG. 6 depicts a flowchart representation of one variation of a method for generating a joint radiotherapy treatment plan that comprises jointly optimizing ITRS and ETRS radiation dose and adapting or adjusting the ITRS radiation dose and/or ETRS dose for a future treatment session.

FIG. 6 is a flowchart depiction of one variation of a method (600) for generating a joint radiotherapy treatment plan that comprises jointly optimizing ITRS and ETRS radiation dose and adapting or adjusting the ITRS radiation dose and/or ETRS dose for a future treatment session. Method (600) may comprise acquiring (602) patient anatomical data (e.g., CT image data), determining (604) patient organ contours, acquiring (606) imaging scans (e.g., functional imaging scans), determining (608) prescription and organ dose constraints, determining (610) the number of fractions or treatment sessions during a treatment period, and calculating (612) dosimetry of a radionuclide (or any desired ITRS) from the functional imaging scan(s). Optionally, the functional image data, anatomical image data, prescribed dose requirements, and RN dosimetry data may be provided (614) to a treatment planning system, which may comprise software code that is executable by a treatment planning controller having one or more processors. In some variations, treatment planning analyses and calculations (602-616) of method (600) may be performed directly using the treatment planning system. Method (600) may further comprise jointly optimizing (616) RN dose and ETRS dose using any of the methods described herein to generate a joint radiotherapy treatment plan that specifies a dose to be delivered by the RN and a dose to be delivered using the ETRS (e.g., any EBRT system, BGRT system). In some variations, the joint radiotherapy treatment plan comprises a delivery fluence map and/or machine instructions for an EBRT system and injection volume for a specified type of RN or radiopharmaceutical. Determining (610) the number of fractions or treatment sessions in a treatment period may comprise calculating the number of ETRS sessions based on a set number of RN session(s), and/or calculating the number of RN sessions based on a set number of ETRS session(s). The total number of sessions, and/or the number of each type of session (i.e., ETRS session, RN session) may be set by a clinician or a clinic policy, and/or may be calculated by the treatment planning system. The clinician may use clinical trial data to determine the optimal fractionation scheme for a given indication. Additionally, the clinician may be histological or diagnostic blood test information to measure the aggressiveness of the tumor. A more aggressive tumor may have a higher dose per fraction for either ETRS or RN, or more fractions to achieve a higher BED dose. Also, the clinician may adjust the fractionization scheme to reduce toxicity to a given OAR. For the treatment planning system to automatically calculate the number of fractions or treatment sessions, a tumor control probably model (TCP) and a normal tissue complication model (NTCP) may be used for each of the patient target regions and the tissues in the patient. The TCP and NTCP models can be used to derive a recommend fractionization scheme to the clinician. Alternatively, the patient may have been treated previously and this information may be used to determine the number of fractions.

Method (600) may optionally comprise treating the patient according to the joint radiotherapy plan. For example, method (600) may comprise delivering (618) one or more treatment sessions or fractions using an EBRT system, and injecting (620) the patient with the calculated dose of RN in one or more treatment sessions. In some variations, method (600) may optionally comprise waiting (622) for the RN to decay and determining (624) whether treatment period is over (i.e., whether the prescribed dose has been delivered, whether all treatment sessions in a treatment period have been completed). Method (600) may comprise acquiring (628) additional or updated functional image data (e.g., functional imaging scans), calculating (630) updated dosimetry of the RN based on the additional or updated functional image data, and jointly optimizing (634) RN dose and/or ETRS/EBRT dose based on the updated RN dosimetry. Optionally, the previously delivered EBRT and RN dose may be imported (632) into the treatment planning system and incorporated into the joint optimization (634). This may also include toxicity data that may be used to generate OAR constraints. Method (600) may then comprise delivering the re-optimized RN and/or ETRS dose to the patient, i.e., delivering (618) the updated EBRT dose in another treatment session, and injecting (620) the updated RN dose in a further treatment session). The acquisition of additional functional images, updating RN dosimetry, jointly re-optimizing RN and/or EBRT dose and delivering the updated doses may be repeated throughout a treatment period as many times as desired. For example, updating/adapting the RN and/or EBRT dose may occur after each treatment session, after every second treatment session, after every RN treatment session (e.g., directly after RN injection, after the RN has decayed), halfway through the treatment period (e.g., after half of the prescribed treatment sessions have been completed), etc. In some variations, updating/adapting the RN and/or EBRT dose may comprise changing the number of RN and/or EBRT treatment sessions in the treatment period. For example, the overall number of treatment sessions may be decreased or increased, and/or the numbers of RN and/or EBRT treatment sessions may be decreased or increased.

As described above, some variations of joint optimization iterate on RN/ITRS dose and ETRS dose to attain a cumulative dose distribution that falls within the bounds of the prescribed dose distribution bDVH. Adapting the RN and/or ETRS radiation dose for a future delivery session may comprise re-optimizing (634) based on the prescribed dose distribution bDVH and may generate a set of DVH curves that are within the bounds of the prescribed dose bDVH, as described above. In some variations, the upper and lower bounds of the prescribed dose bDVH may be updated before re-optimization (634). The upper and lower bounds may be updated to account for the dose that has already been delivered and/or the dose yet-to-be-delivered, and the updated upper and lower bounds of the prescribed dose bDVH may be different from the upper and lower bounds of the prescribed dose bDVH for the first joint optimization. That is, the nominal prescribed dose distribution may be the same across both joint optimizations, but the upper and lower bounds may be different. For example, the range of acceptable deviations from the nominal dose distribution may be wider for a first joint optimization than for a second joint optimization that occurs after one or more treatment sessions. A tighter tolerance on later-delivered dose may help ensure that the overall delivered dose for the entire treatment period (i.e., over multiple treatment sessions) converges to the prescribed dose distribution. For example, incorporating updated RN dosimetry (630) and/or doses from previous external beam and/or RN treatment sessions (632) into joint re-optimization (634) may optionally comprise updating the upper bounds and lower bounds of the prescribed dose distribution bDVH based on the updated RN dosimetry and/or previously delivered doses, and iterating on RN dose and ETRS dose to derive a cumulative dose that falls within the updated boundaries of the bDVH.

Methods for Adapting Radionuclide Dose Between Treatment Periods

After a treatment period has ended (i.e., all of the jointly optimized and planned ITRS dose and ETRS dose has been delivered), imaging data (e.g., functional imaging data) may indicate that some tumors responded to the treatment (e.g., by reducing in size or being eliminated altogether) while other tumors did not respond (e.g., little, if any, changes in size and/or metabolic activity). Imaging data may reveal the presence of additional tumors (i.e., tumors that were unknown when the first treatment period was planned). In some variations, a second treatment period may be added to address the non-responsive or new tumors. The treatment planning and joint optimization for the second treatment period may be similar to the methods described and depicted in FIGS. 3, 4, 6, 7A-7B (which will be described below) and may include updates to the dose prescription and optimization constraints. In some variations, the joint treatment planning and optimization for the second treatment period may comprise calculating the dosimetry of different radionuclides and compounds, different dose structures, adjusted OAR cost functions (or constraints) to reflect the effects of the radiation delivered in the previous treatment period. For example, a first treatment period may deliver radiation to a patient using a first RN compound (e.g., RN1-Target1) in conjunction with EBRT, which have been jointly optimized. Imaging data taken at the end of the treatment period may show that a subset of tumors did not respond to the radiation delivered during the first treatment period. This imaging data, along with toxicity data, delivered dose data, and the like may be incorporated into the generation of a treatment plan for a second treatment period. For this treatment plan, a second RN compound may be used (e.g., RN2-Target1, RN1-Target2), depending on the characteristics of the non-responsive tumors. For example, the targeting backbone of the ITRS may be changed from the first treatment period to another targeting backbone that may be more specific to the non-responsive tumors (e.g., to target cellular markers specific to those tumors) and/or to have higher affinity or uptake by the non-responsive tumors. Alternatively, or additionally, a higher-energy RN may be selected. In some variations, the ETRS dose distribution may be adjusted to address non-responsive tumors. Constraints for one or more OARs may be tightened for one or both ITRS and ETRS dose to help reduce toxicity to the OAR(s). This second ITRS dose may be jointly optimized with the ETRS dose, and the constraints on the ETRS dose may be adjusted to be complementary to the dose distribution of the second RN compound. The number and type of treatment sessions in the second treatment period may be adjusted from the number and type of treatment sessions in the first treatment period. The treatment plan may be delivered in the second treatment period in a similar manner as previously described for the first treatment period, and may optionally include inter-fraction adaptations or updates (i.e., adaptations or updates between treatment sessions).

Methods for Joint Internal Radionuclide Therapy (IRT) and Biologically-Guided Radiation Therapy (BGRT)

Methods for generating a joint radiotherapy treatment plan for combined internal radionuclide therapy (IRT) and biologically-guided radiation therapy (BGRT) may jointly optimize the RN dose and BGRT dose using the same set of image data. For variations of BGRT that use PET data to guide real-time radiation delivery, the image data (e.g., functional image data) acquired during treatment planning may use a PET tracer that has the same targeting backbone as the radiopharmaceutical that is injected or implanted into the patient for radiotherapy. During a BGRT treatment session or fraction, the patient may be injected with the same PET tracer that was used to generate the planning image and external-beam radiation may be directed to the patient target region(s) based on the PET data acquired during the BGRT treatment session. A RN treatment session may follow the BGRT treatment session, where a radiopharmaceutical that has the same targeting backbone as the PET tracer may be injected into the patient. While the injected radiopharmaceutical may have the same targeting backbone as the PET tracer used for imaging, the radionuclide may not be a positron-emitting radionuclide and may instead be a radionuclide that emits different (e.g., higher) energy levels and/or particles for the therapeutic irradiation of a patient target region. In some variations, the PET data acquired during a BGRT treatment session may be used to adapt or modify the amount of radiopharmaceutical that is injected into the patient during a RN treatment session. The adaptation may be scaling the volume of radiopharmaceutical dose based on any changes in patient toxicity, and/or may include re-optimizing the RN dose using any of the optimization methods described herein. Alternatively, or additionally, image data may be acquired outside of a BGRT treatment session, and this image data may be used to adapt or modify the amount of radiopharmaceutical that is injected into the patient during a RN treatment session. Optionally, RN and BGRT dose distributions for a future treatment session may be jointly re-optimized according to PET data acquired during or after a previous treatment session.

While the variations described herein relate to radionuclides that emit positrons (i.e., PET tracers or radiopharmaceuticals), it should be understood that these methods may be also be used for any suitable radionuclides, for example, single-photon emitting radionuclides (e.g., SPECT) tracers or radiopharmaceuticals.

Figure 7A:
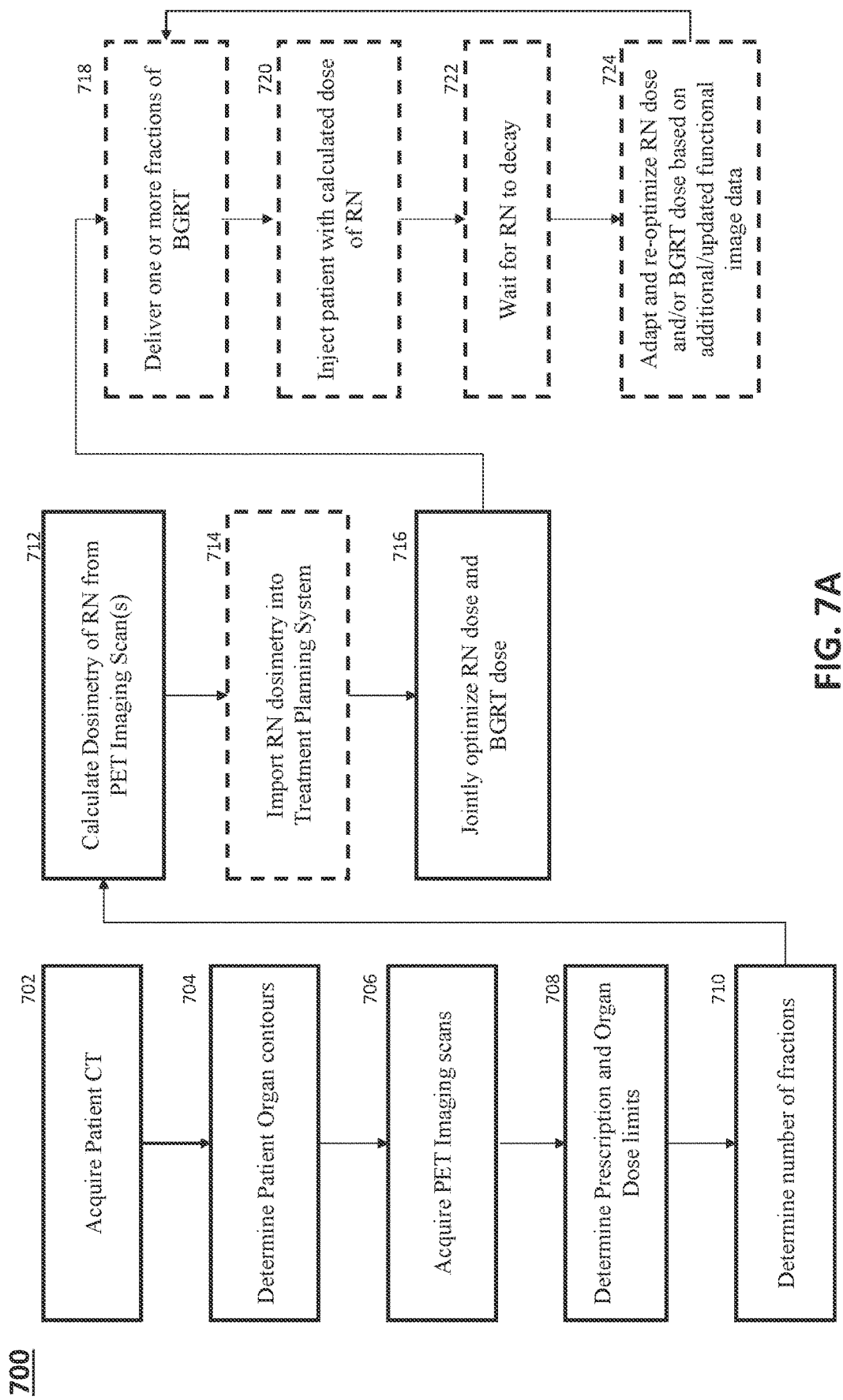
FIG. 7A depicts a flowchart representation of one variation of a method for generating a joint radiotherapy treatment plan that comprises jointly optimizing RN radiation dose and BGRT radiation dose and optionally, adapting or adjusting the RN radiation dose and/or BGRT dose for a future treatment session.

FIG. 7A is a flowchart depiction of one variation of a method (700) for generating a joint radiotherapy treatment plan that comprises jointly optimizing RN radiation dose and BGRT radiation dose and optionally, adapting or adjusting the RN radiation dose and/or BGRT dose for a future treatment session. Method (700) may comprise acquiring (702) patient anatomical data (e.g., CT image data), determining (704) patient organ contours, acquiring (706) PET imaging scans, determining (708) prescription and organ dose constraints, determining (710) the number of fractions or treatment sessions during a treatment period, and calculating (712) dosimetry of a radionuclide or radiopharmaceutical from the PET imaging scan(s). Optionally, the PET image data, anatomical image data, prescribed dose requirements, and RN dosimetry data may be provided (714) to a treatment planning system, which may comprise software code that is executable by a treatment planning controller having one or more processors. In some variations, treatment planning analyses and calculations (702-716) of method (700) may be performed directly using the treatment planning system. Method (700) may further comprise jointly optimizing (716) RN or radiopharmaceutical dose and BGRT dose using any of the methods described herein to generate a joint radiotherapy treatment plan that specifies a dose to be delivered by the RN or radiopharmaceutical and a dose to be delivered using the BGRT system. Method (700) may also output one or more firing filters (e.g., shift-invariant firing filters) that may be used in conjunction with PET image data acquired during a BGRT treatment session to irradiate patient target regions. Determining (710) the number of fractions or treatment sessions in a treatment period may comprise calculating the number of BGRT sessions based on a set number of RN session(s), and/or calculating the number of RN sessions based on a set number of BGRT session(s). The total number of sessions, and/or the number of each type of session (i.e., BGRT session, RN session) may be set by a clinician or a clinic policy, and/or may be calculated by the treatment planning system, as previously described. For example, the clinician may use clinical trial data to determine the optimal fractionation scheme for a given indication, and/or may adjust the fractionation scheme to reduce toxicity to a particular OAR. Alternatively, or additionally, TCP and NTCP models may be used to derive a recommended fractionation scheme to the clinician.

Method (700) may optionally comprise treating the patient according to the joint RN and BGRT radiotherapy plan. For example, method (700) may comprise delivering (718) one or more treatment sessions or fractions using a BGRT system, and injecting (720) the patient with the calculated dose of radiopharmaceutical in one or more RN treatment sessions. In some variations, method (700) may optionally comprise waiting (722) for the radiopharmaceutical to decay. Method (700) may comprise adapting (724) the radiopharmaceutical dose and/or BGRT dose based on additional image data (e.g., functional image data). The additional image data may be acquired during an additional imaging session that occurs between treatment sessions, and/or during the BGRT treatment session. Adapting the radiopharmaceutical and/or BGRT dose may comprise joint re-optimization, as described above (e.g., steps (628-634) of method (600) depicted in FIG. 6). The acquisition of additional images, updating RN dosimetry, jointly re-optimizing RN and/or BGRT dose and delivering the updated doses may be repeated throughout a treatment period as many times as desired. For example, updating/adapting the RN and/or BGRT dose may occur after each treatment session, after every second treatment session, after every RN treatment session (e.g., directly after RN injection, after the RN has decayed), halfway through the treatment period (e.g., after half of the prescribed treatment sessions have been completed), etc.

One variation of jointly adapting and re-optimizing (724) RN and BGRT radiation doses may comprise acquiring image data (e.g., functional image data) to update pharmacokinetic models of RN dose distribution, calculating an updated dosimetry of the RN based on the updated pharmacokinetic models, and jointly re-optimizing the RN and BGRT radiation doses using the updated RN dosimetry data. Image data may include PET imaging data acquired during a BGRT treatment session, and/or gamma camera imaging data acquired during a RN treatment session (e.g., after RN injection, but before RN decay). Optionally, image data may include imaging data acquired during an imaging session separate from a treatment session, such as a diagnostic imaging session. These newly-acquired image data may be used to update RN dosimetry so that the joint re-optimization may reflect the deliverable RN dose more accurately and/or account for any patient physiological changes that may affect RN dose distribution and pharmacokinetics. Alternatively, or additionally, jointly adapting and re-optimizing (724) RN and BGRT radiation doses may output one or more adapted (e.g., updated) firing filters (e.g., shift-invariant firing filters). When these updated firing filters are used in conjunction with PET image data acquired during the BGRT treatment session, the therapeutic radiation may deliver a different dose of radiation to the patient target regions, thereby responding to changes in the patient's physiological and/or disease state.

Figure 7B:
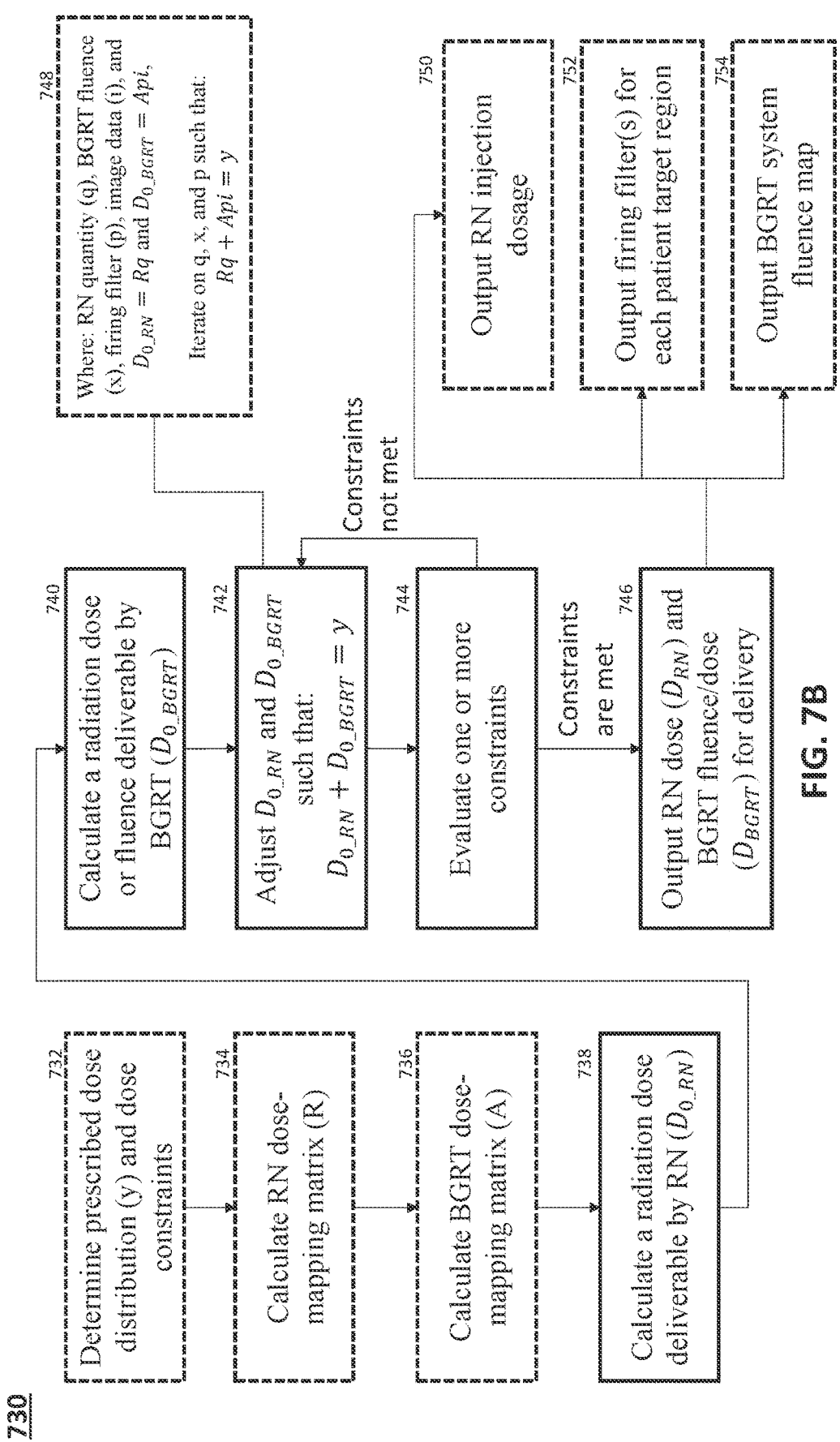
FIG. 7B depicts a flowchart representation of one variation of a method for joint optimization of RN radiation dose and BGRT radiation dose. BGRT treatment planning includes the calculation of one or more firing filters p.

FIG. 7B depicts one variation of a method for joint optimization of RN radiation dose and BGRT radiation dose. This method may be used in the original joint optimization and optionally, for any successive joint re-optimizations. BGRT treatment planning includes the calculation of one or more firing filters p. A firing filter may be a matrix or mapping operator that designates the conversion from image data to a radiation fluence map, where fluence map may include radiation beamlet pattern and/or beamlet intensities to be applied to the patient during a treatment session. A firing filter p may be shift-invariant. During a BGRT treatment session, firing filters p may be applied (e.g., convolved, multiplied) to image data acquired during the treatment session to calculate the delivery fluence. The image data may comprise low-signal, partial, PET images that may be acquired during short time windows (e.g., about 1 second, about 500 ms or less). In some variations, such image data may be referred to as limited time sampled (LTS) images. The calculated delivery fluence may be segmented into BGRT machine instructions, in real-time, to irradiate the patient target region during the BGRT treatment session. Conceptually, a firing filter (p) represents the relationship between a fluence map x for radiation delivery to a patient region and an image i of that patient region; that is:

$$x = p \cdot i$$

A firing filter p may be calculated as part of joint optimization of the radiopharmaceutical dose and BGRT dose, as depicted in FIG. 7B and described below. Method (730) may comprise calculating (738) a radiation dose that is deliverable by a RN or radiopharmaceutical ($D_{0\_RN}$), calculating (740) a radiation dose that is deliverable by a BGRT system ($D_{0\_BGRT}$), adjusting (742) the RN and BGRT doses ($D_{0\_RN}$, $D_{0\_BGRT}$) to meet the dose prescription (as determined by the clinician), and evaluating (744) one or more prescribed dose requirements (e.g., constraints). If the prescribed dose requirements are not met, method (730) then comprises iteratively adjusting the RN and BGRT dose distributions ($D_{0\_RN}$, $D_{0\_BGRT}$) until the requirements at met. After the dose requirements are met, method (700) may comprise outputting (746) the RN dose ($D_{RN}$) and BGRT dose ($D_{BGRT}$) for delivery during one or more treatment sessions. In some variations, method (700) may comprise outputting one more of RN injection dosage (750), one or more firing filters for each patient target region (752), and/or a BGRT system fluence map (754). A BGRT system fluence map may contain the fluence values that are deliverable by a BGRT system.

In some variations, method (730) may optionally comprise determining (732) the prescribed dose distribution (y) and dose constraints to the patient, calculating (734) RN dose-mapping matrix (R), and calculating BGRT dose-mapping matrix (A), which may be used to adjust or iterate (742) on the RN and BGRT doses ($D_{0\_RN}$, $D_{0\_BGRT}$). The prescribed dose distribution may be the cumulative radiation dose to the patient as specified by a clinician and may be represented by a vector of voxels (y) in the patient, each voxel having a dose value. Calculating (734) the RN dose-mapping matrix (R) may comprise determining the relationship between the volume of an injected or implanted RN and its delivered dose. In some variations, radionuclide dosimetry is performed for a fixed injection volume, and the dosimetry of a radionuclide treatment may be generally linearly related to the amount of radionuclide that is injected. Calculating (734) the RN dose-mapping matrix (R) may comprise mapping one or more images (I) (e.g., functional images) to the biologically-equivalent absorbed dose Gy per unit of an injected RN. The images may be acquired using an imaging tracer that has a carrier molecule or targeting backbone that is the same as the carrier molecule or targeting backbone for the RN or radiopharmaceutical. This mapping (F) may be given by:

$$F\left(I\left[\frac{kBq}{ml}\right]\right) = R\left[\frac{Gy}{kBq}\right]$$

The RN radiation dose ($D_{0\_RN}$) that is capable of being delivered to the patient may be represented by a similar linear relationship as the injected dose scalar (q, which may, more generally, be a quantity of RN) multiplied by the RN dose-mapping matrix (R), which maps the injected dose (q) to the voxelized dosimetry $D_{0\_ITRS}$. That is:

$$D_{0\_RN} = q$$

Any of the RN dosimetry methods described above may be used to calculate (734) the ITRS dose-mapping matrix (R). Alternatively, or additionally, the RN dosimetry may be non-linearly related to the amount of injected RN and may incorporate time-variant pharmacokinetics of the RN (e.g., where at high injection volumes, the RN has a physiologic effect on the patient that is independent of the ionization radiation). The time-variant pharmacokinetics may be specific to the patient or derived from population averages. Also, time-variant pharmacokinetics may be updated from functional imaging scans acquired during treatment. Then for further adaptive treatments, the time-variant pharmacokinetics can be updated using the most recent function scan information.

The time-variant pharmacokinetics may be derived from other methods besides functional imaging. For example, time-variant pharmacokinetics may be derived from a blood sample or multiple blood samples before and after injection. Alternatively, or additionally, time-variant pharmacokinetics may be derived from measuring excreted radioactivity in the urine.

Optionally, in some variations, an ITRS may comprise two different radiopharmaceuticals. The total ITRS dose may be represented by a first injection of a first radionuclide ($q_1$) and a second injection of a second radionuclide ($q_2$). The first and second radiopharmaceuticals may be injected simultaneously or sequentially into the patient. Each radiopharmaceutical may have a different dose mapping matrix ($R_1$, $R_2$), but the doses sum linearly. The total RN dose may be calculated as described above with reference to FIG. 4.

The BGRT dose ($D_{0\_BGRT}$) deliverable to the patient may be modeled as a linear system and calculated by multiplying the BGRT dose-mapping matrix (A) with the deliverable BGRT fluence (x), where the deliverable BGRT fluence (x) is given by the firing filter (p) multiplied (or convolved with) the planning image (i) (which may be a functional image):

$$D_{0\_BGRT} = Ax = Api$$

Iterating (742-744) RN and BGRT dose distributions may comprise scaling the RN and BGRT doses into a dose space that is equivalent to the prescription dose space (748), and iterating on RN quantity (q) and firing filter (p). In some variations, the prescription dose, RN dose and BGRT dose may all be defined in the BED space. The sum of RN and BGRT doses in the BED space ($D_{cumulative}$) should be the radiation dose prescribed by the clinician, i.e., the prescribed dose distribution (y):

$$D_{cumulative} = y, \text{ where}$$

$$D_{cumulative} = D_{0\_RN} + D_{0\_BGRT} = Rq + Api$$

In addition to requiring that the RN and the BGRT radiation dose sum to the prescribed dose distribution, prescribed dose requirements may comprise a set of constraints on all the prescription objectives. In some variations, these constraints may be convex constraints. These convex constraints may imposed on the BGRT fluence (x) and/or firing filters (p), on the RN quantity (q), on the dose deliverable by the RN ($D_{0\_RN}$), on the dose deliverable by the BGRT ($D_{0\_BGRT}$), and/or on the cumulative dose ($D_{cumulative} = D_{0\_RN} + D_{0\_BGRT}$). An example of a convex constraint which may be unique to joint optimization is the minimum dose on the patient target region (e.g., PTV) where $D_{cumulative} = D_{0\_RN} + D_{0\_BGRT}$, does not exceed a predefined dose value (in Gy). The ITRS quantity (q) may be constrained to be within a range of acceptable quantities (i.e., q must be within a specified range), and/or may be constrained such that it is an integer multiple of quantized steps. For example, for practical reasons on dosage, the ITRS quantity may be only available in certain discrete dosages. The joint optimization may then have to optimize the injected dose (q) over a limited set of fixed dosages.

In some variations, these constraints may be weighted by a linear factor that defines or approximates their relative importance. For example, dose constraints may comprise one or more cost functions, and optionally, each cost function may be weighted by an individual scaling factor. Prescribed dose requirements or constraints (C) may comprise one or more cost functions and may include, for example, one or more of a cost function C(x) on radiation fluence (x) and/or firing filter (p), and/or a cost function C(q) on RN quantity (q), and/or a cost function C(Api) on $D_{0\_BGRT}$, and/or a cost function C(Rq) on $D_{0\_RN}$, and/or a cost function C($D_{cumulative}$). These may each optionally be weighted by an individual scaling factor ($w_i$, $w_j$, $w_k$, $w_l$, $w_m$). For example, a cost function on the fluence can be used to optimize treatment time in the context of joint delivery. Optionally, a cost function on the ETRS dose may be included to limit skin dose and/or radiation burn toxicity. For example, a cost function on the injected dose (q) can be optimized ensuring that the dose value is one that may be feasible to be prepare and introduce into the patient. For example, a cost function of $D_{0\_RN}$ might optimize hematological toxicity (e.g., a cost function that prioritizes the preservation of white blood cells) independent of ETRS dose. Another example is a cost function imposed on the cumulative ITRS and ETRS dose $D_{cumulative}$ that limits the mean combined dose to the heart.

$$C = \Sigma w_i C_i(x) + \Sigma w_j C_j(q) + \Sigma w_k C_k(Api) + \Sigma w_l C_l(Rq) + \Sigma w_m C_m(D_{cumulative})$$

In some variations, optimization constraints may be met based on a priority ranking. For example, each dose constraint may be ranked, and during optimization, constraints may be satisfied or met based on the corresponding priority ranking. For example, in joint optimization, RN constraints may be prioritized over BGRT constraints or vice versa. Alternatively, for example, the constraints may be prioritized based on organ system so that different BGRT constraints and RN constraints may have different priority rankings.

Methods of joint optimization may optionally comprise defining dose constraints where one or more cost functions are designated as high-priority (e.g., mandatory) cost functions, and designating the other cost functions as low-priority (e.g., optional) cost functions. The high-priority cost functions may be assigned the highest possible weight and/or priority ranking, and the low-priority cost functions may be assigned a lower weight and/or priority ranking. In some variations, the high-priority cost functions may have more "stringent" constraints, while the low-priority cost functions may have more "lax" constraints. For example, a high-priority cost function may tightly limit irradiation of the heart (or any desired OAR) to a range that is less than 1 Gy, while a low-priority cost function may limit irradiation of the tissue around a patient target region to a broader range of no more than 5 Gy. In some variations, the clinician may prioritize bone marrow toxicity over potential toxicity to the pancreas. For example, the constraints on the bone marrow must be met before any constraints on the pancreas are evaluated. In some variations, the clinician may set the weight(s) and/or priority ranking(s) of the high-priority cost functions, and based on this clinician input, the treatment planning system/optimizer may auto-calculate the weight(s) and/or priority ranking(s) of the lower-priority cost functions. During joint optimization, the cumulative RN and/or BGRT dose must satisfy the high-priority cost functions at the specified weight and/or priority ranking (e.g., reduce the value of any high-priority penalty functions), while the low-priority cost functions may be satisfied at varying lower weights and/or priority rankings. For example, the range of acceptable values of low-priority cost functions may be wider than the range of acceptable values of high-priority cost functions. The weights and/or priority rankings of the low-priority penalty functions may be adjusted (e.g., automatically adjusted and/or calculated) relative to each other in order to meet the prescribed dose constraints or requirements. The acceptable ranges may be specified by the clinician and/or calculated by the treatment planning system (and may be subject to clinician review and/or approval).

As described previously, some methods of joint optimization may optionally display a set of clinical objectives to a clinician, and the specific dose constraints and cost functions for guiding joint optimization may be defined based on the clinical objectives that are selected by the clinician. Specifying one or more clinical objectives may facilitate the definition of dose constraints and/or setting of specific cost functions for clinicians, and reduce the setup time for treatment planning and joint optimization. In addition, defining dose constraints based on clinical objectives may promote ease-of-use and comprehensibility of the treatment planning system for a broader range of clinicians, including but not limited to, radionuclide specialists and radiation oncologists. This may help ensure that the patient's treatment goals and needs are met, and help ensure that organs-at-risk are correctly defined for the treatment planning system. In one variation, each clinical objective may be linked to one or more cost functions. Some clinical objectives may be specific to an ETRS (e.g., radiation delivered by an EBRT system) or an ITRS (e.g., radiation delivered by a radionuclide or brachytherapy), while some clinical objectives may be applicable to any type of therapeutic radiation (e.g., the combined effects of ETRS and ITRS dose). For example, clinical objective(s) that involve skin dose and/or radiation burn toxicities may be used to define dose constraints for the ETRS (but not necessarily the ITRS), while clinical objective(s) that involve blood toxicities linked to perfusion rates and/or distribution kinetics may be used to define dose constraints for the ITRS (but not necessarily the ETRS). In some variations, an example of a clinical objective (that may be applicable to both ETRS and ITRS dose) could be control of all tumors greater than 1 cm by having a cost function on the minimum dose on the PTV that must be greater than 50 Gy. In some variations, an example of a clinical objective could be to limit the probability of grade 2 kidney toxicity to less than 10% by linking that to a cost function that limits the maximum kidney dose to less than 40 Gy. Optionally, when multiple clinical objectives are selected, the clinician may be able to assign a priority or weight to each clinical objective relative to the other clinical objectives (e.g., set a priority ranking for each clinical objective). Joint optimization may then iterate on RN dose and BGRT dose to meet dose constraints and/or cost functions that have been prioritized and/or weighted according to their corresponding clinical objective.

In some variations of methods for joint optimization, a convex optimizer may be used to solve for the optimal BGRT fluence (x) and/or firing filter (p), and the optimal injected RN dose (q) given dose constraints that comprise one or more of the above cost functions. The optimization may be performed, evaluated, and analyzed in a treatment planning system, and approved by a clinician. Additional details regarding BGRT treatment planning and delivery methods may be found in U.S. patent application Ser. No. 15/993,325, filed May 30, 2018, which is hereby incorporated by reference in its entirety.

In some variations, a BGRT firing filter (p) may be generated such that BGRT radiation delivery is reduced to areas in an image that have higher RN dose values. For example, BGRT dose to areas where PET data intensity (e.g., standard uptake value or SUV) exceeds a threshold may be scaled back while BGRT dose to areas where PET data intensity or SUV is at or below a threshold is increased (e.g., not scaled back). For example, an area in a patient target region that has relatively high RN dose values may be considered a "hot spot", and BGRT dose to that area may be lowered accordingly.

In some variations, the prescribed dose distribution (y) may be represented by a bounded dose-volume histogram (bDVH) having a nominal prescribed dose curve and any dose delivery uncertainty is represented by an upper bound curve and a lower bound curve. The upper and lower bounds of the prescribed dose distribution bDVH may be calculated based on uncertainties and/or variabilities in radiation dose delivered by a RN and/or a BGRT. For example, BGRT dose delivery uncertainties and/or variabilities may arise from patient motion (e.g., respiratory motion, cardiac motion, physiologic motion that may alter the position of the patient target region during radiation delivery), high-energy radiation source precision and/or accuracy, PET tracer injection variabilities, and the like. Since the dose provided by a RN may be calculated using a functional imaging scan, any variance in the scan may cause variance in the dose estimate. Imaging scan uncertainties and/or variabilities may arise from variations in blood flow rate, perfusion distribution, pharmacokinetics, binding specificity of the targeting backbone, injection dose measurement and the like. Also, the dose may vary due to infusion variabilities of the radiopharmaceutical in the patient. RN dose delivery uncertainties and/or variabilities may arise from variations in blood flow rate, perfusion distribution, pharmacokinetics, binding specificity of the targeting backbone, injection dose measurement uncertainty, BED modelling errors and the like. Other ITRS dose variabilities may arise from changes in the patient's physiological or biological state. For example, there may be changes in the patient's metabolism and/or gastrointestinal state (e.g., constipation, gastritis, etc.) that may alter the rate and manner in which an injected or ingested RN or radiopharmaceutical is excreted. If a patient is having gastric issues, a greater percentage of a RN may be excreted through the urinary tract instead of the gastrointestinal tract. There may also be interactions between other medications taken by the patient and the RN or radiopharmaceutical that may affect the ITRS dose and kinetics. BGRT and RN dose uncertainties may be combined to derive the upper bound of delivered dose and the lower bound of delivered dose. In some examples, the upper and lower bounds may be derived using models of BGRT and/or RN dose uncertainties so that interactions between different uncertainties may be represented in the boundaries of bDVH. Iterating (742-744, 748) on RN and BGRT doses in the BED space may comprise adjusting one or both of the $D_{0\_RN}$ and $D_{0\_ETRS}$ such that the DVH of the cumulative dose ($D_{cumulative}$) is within the upper and lower bounds of the prescribed dose distribution (y) bDVH. In some variations, this may comprise iterating on RN quantity (q) and/or BGRT fluence (x) until the DVH of the cumulative dose ($D_{cumulative}$) is within the upper and lower bounds of the prescribed dose distribution (y) bDVH. The output or result of jointly optimizing RN and BGRT doses may comprise one or more DVH curves that represent one or more cumulative doses (i.e., a range of cumulative doses) that are within the upper and lower bounds of the prescribed dose distribution (y) bDVH. The output of jointly optimizing ITRS and ETRS doses may comprise one or more solutions to the same optimization problem set with different local minima for non-target volumes. For example, if there are three cost functions participating at low cost for different OARs in the optimization that would achieve the target prescription dose equally well, the optimizer may produce DVH curves and dose distributions for each of these results for the clinician to choose between. In all three cases, the prescription dose is met equally well, but the individual doses for OARs may differ substantially. In some variations, the joint optimization may generate a set of DVH curves for the optimized cumulative doses that fall within the upper and lower bounds of the prescribed dose distribution bDVH. Evaluating (744) the constraints may optionally include clinician evaluation and/or selection of a particular dose distribution based on the DVH curves. For example, this set of DVH curves may be displayed to the clinician, along with the individual RN dose and the BGRT dose for each of the DVH curves, and the clinician may select one of the DVH curves and its corresponding RN and BGRT doses for delivery. For example, in a set of DVH curves that meet the prescribed dose requirements and/or fall within the bounds of the prescribed dose bDVH for a patient target region, the dose to one or more OARs may vary, and as part of evaluating the jointly optimized dose distributions, a clinician may select the dose distribution that delivers less radiation dose to a particular OAR as compared to other dose distributions. After evaluation of the possible radiation doses for delivery based on dose constraints/requirements and/or clinician selection, the joint optimizer may output (746) the RN dose and the BGRT fluence/dose that is to be delivered during a treatment period.

In some variations, a joint RN and BGRT radiation treatment period may comprise a BGRT treatment session, a RN treatment session, an inter-session gap, and then another BGRT treatment session and another RN treatment session. This may be repeated until the prescribed number of BGRT and RN treatment sessions in the treatment period is completed. The inter-session gap may be any desired duration of time, for example, a few hours (e.g., 1 hour, 2, hours, 3 hours, 4 hours, 6 hours, 8 hours, etc.), a few days (e.g., 1 day, 2 days, 3 days, 5 days, 6 days, etc.) or a few weeks (e.g., 1 week, 1.5 weeks, 2 weeks, 3 weeks, 4 weeks or more, etc.). Optionally, the BGRT dose and RN dose for a future treatment session may be jointly optimized, adapted, and/or otherwise modified based on additional functional image data and/or patient data. The adapted BGRT and/or RN dose may reflect changes in patient toxicity, disease state, patient well-being, mood, physiological function.

Radiopharmaceutical Compounds for Imaging and Radiotherapy

Various radionuclides and radiopharmaceutical compounds may be used for imaging (e.g., functional imaging, molecular imaging, nuclear imaging, etc.) of the patient and/or as an internal therapeutic radiation source. Methods may comprise acquiring image data (e.g., functional image data) using a radiopharmaceutical compound having the same targeting backbone as the radiopharmaceutical compound used for therapy. The radioactive isotope for radiotherapy may be the same or different radioactive isotope that is used for imaging. In some variations, a first radiopharmaceutical compound may be used for a first injection and a second radiopharmaceutical compound could be used for a second injection. The second radiopharmaceutical compound may be different or the same as the first radiopharmaceutical compound. In some variations, radiotherapy treatment may commence with a first radiopharmaceutical compound, but after acquiring and analyzing updated or more recently-acquired image data, a different radiopharmaceutical compound might be selected for later treatment sessions. For example, if updated image data (e.g., biological and/or functional image data) indicates higher than expected levels of toxicity, or an abrupt disease progression, or little or no response to the therapy, a clinician may select a different radiopharmaceutical compound for future sessions, e.g., with less toxicity and/or more targeted or increased radiation delivery. FIG. 8 summarizes several examples of radiopharmaceutical compounds that may be used for image data acquisition and radiotherapy (e.g., targeted radionuclide therapy) in any of the methods described herein. It should be understood that the compounds in the table of FIG. 8 are merely examples, and that the radionuclides in the table may be paired with targeting backbones or carrier molecules other than the ones in the table. Examples of radionuclides that may be used for imaging and/or therapy (either alone or conjugated with a carrier molecule or targeting backbone) may include, but are not limited to PET radionuclides such as NaF-18, F-18, Ga-68, Cu-64, Zr-89, I-124, Sc-44, Tb-152, and Y-86, SPECT radionuclides such as Tc-99m, In-111, Tb-155, and I-123, beta-emitting radionuclides such as Cu-67, Sr-89, Y-90, I-131, Tb-161, and Lu-177, and alpha-emitting radionuclides such as Bi-212, Bi-213, At-211, Ac-225, Th-227, Ra-223, Pb-212, and Tb-149.

Any of the listed radionuclides may be attached to carrier molecules that target (i.e., bind specifically to) prostate-specific membrane antigen (PSMA), fibroblast activation protein (FAP), somatostatin receptors (SSR), somatostatin receptor type 2 (SSTR 2), human epidermal growth factor receptor 2 (HER2), gastrin-releasing peptide receptor (GRPR), C—X—C chemokine receptor type 4 (CXCR4), hydroxyapatite crystals in bone, CD20 antigen, CD22 antigen, CD45 antigen, CD33 antigen, CD37 antigen, CD38 antigen, CD276 antigen, mesothelin (MSLN), hypoxia markers, folate receptor, immune checkpoint proteins such as PD-1, PD-L1, PD-L2, Na/I symporter, calcium-sensing receptors (e.g., a calcimimetic), norepinephrine transporter, and neurotensin receptor 1 (NTSR1). Examples of carrier molecules or targeting backbones that may be used with one or more of the radionuclides above may include, but are not limited to, DOTA-TATE (NETSPOT), DOTA-TOC, PSMA-11, PSMA-617, NeoBOMB1, Pentixafor, iobenguane (MIBG), TCMC trastuzumab, MDP, iodine, ibritumomab tiuxetan, SARTATE, thymidine, methionine, misonidazole (MISO), azomycin-arabinoside, erythronitroimidazole, other nitromidazole derivatives, folic acid, 5F7 antibody, choline, DCFPyL, DCFBC, PD-1 antibody or other PD-1 binding protein, PD-L1 antibody or other PD-L1 binding protein, PD-L2 antibody or other PD-L2 binding protein, satoreotide tetraxetan, lexidronam, tositumomab, apamistamab, lilotomab satetraxetan, omburtamab, 3BP-227 (FAP-2286), fibroblast Activation Protein Inhibitors (FAPI) or other molecules binding to fibroblast activation protein, Girentuximab, and pentixather.

Examples of radiopharmaceutical compounds that may be used in conjunction with EBRT and incorporated in a treatment plan that jointly optimizes both the radiopharmaceutical dose and ETRS dose may include, but are not limited to, radium-223 chloride, Y-90 loaded glass microspheres (which may be resin microspheres), I-131 radioiodine, SM-153 lexidronam, Lu-177 DOTATATE, I-131 mIBG, I-131 aCD45, Lu-177 PSMA-617, Lu-177 NeoBOMB1, Ho-166 microspheres, Lu-177 DTA-JR11, Lu-177 PSMA-R2, Ac-225 aCD38, Ac-225 aCD33, Th-227 MSLN-TTC, Th-227 PSMA-TTC, Th-227 CD22-TTC, Lu-177 CTT-1403, I-131 CLR131, I-131 CLR1404, Ac-225 FPX-01, Sm-153 CycloSam, Pb-212 DOTAMTATE, Lu-177 RM2, Th-225 HER2-TTC, Pb-212 PLE, Pb-212 aTEM1, Pb-212 aCD37, At-211 aLAT-1.

Brachytherapy

While the examples described herein pertain to the use of radionuclides, it should be understood that similar methods and workflows may use any agent or device configured to be injected or implanted into a patient that emits radiation internally (i.e., where the therapeutic radiation is emitted from within the patient body). For example, the methods and workflows described herein may be used with brachytherapy devices and methods. One variation of a brachytherapy device may comprise radioactive tubes or wires, and the radiotherapy treatment plan may further specify the implantation location of the tubes or wires, the number of tubes or wires, the implantation time, and/or the radioactivity levels of the tubes or wires. The radioactive tubes or wires may be temporarily inserted into the patient using one or more catheters, and in some variations, under robotic control.

Another variation of a brachytherapy device may comprise a radioactive portion (e.g., seeds or microspheres) and a housing disposed over the radioactive portion. The housing may be sized and shaped to accommodate the anatomical structures at the implantation location so that the radioactive portion is positioned at the location specified by the joint radiotherapy treatment plan. Some methods may comprise using both injectable RN and brachytherapy devices are used for treatment, and those methods may comprise acquiring functional images of both the brachytherapy device(s) and the injected RN to obtain dosimetry data. The dosimetric data from such functional images may be used to adapt and/or re-optimize the ITRS dose and ETRS dose for future treatment sessions. It should be understood that functional images may also be acquired of only the brachytherapy devices for dose calculations, treatment delivery adaptation and/or re-optimization.

External Beam Radiation Therapy Systems

Figures 9A, 9B:
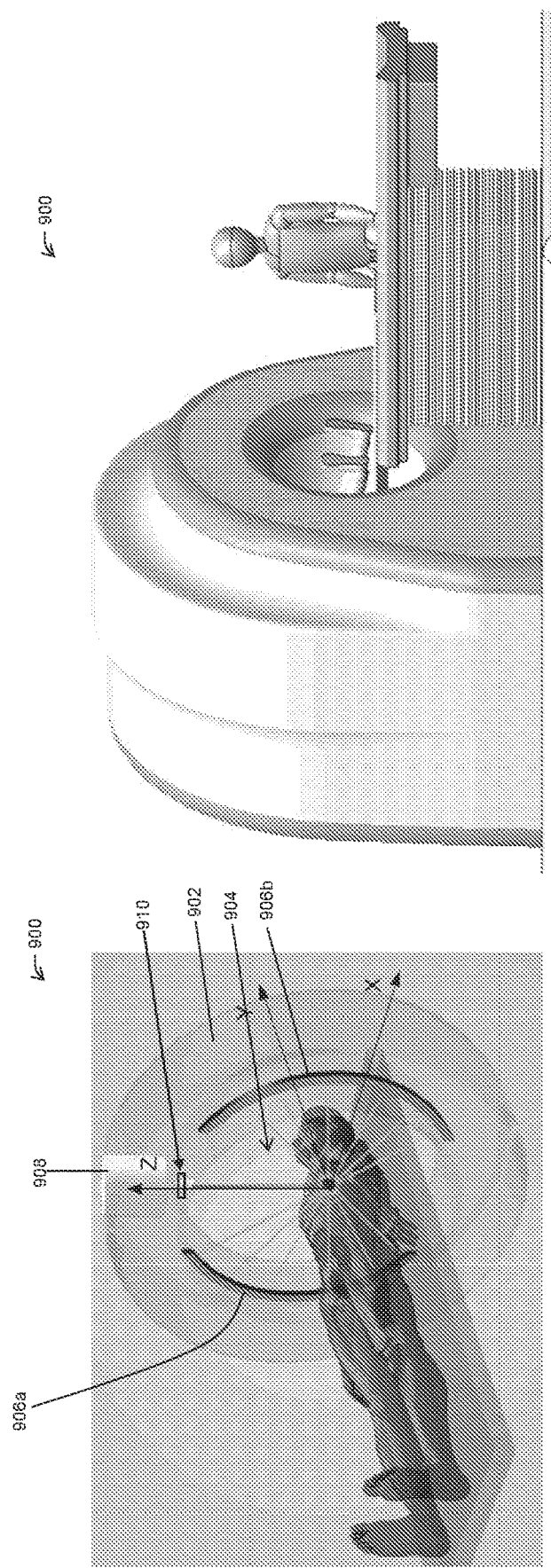
FIGS. 9A-9B depict one variation of a radiotherapy system.

An external therapeutic radiation source may be part of a radiotherapy system that comprises components for the control and use for the external therapeutic radiation source, and in some variations, may be an external beam radiation therapy system. FIGS. 9A-9B depict one variation of a radiotherapy system that may be used for joint radiopharmaceutical and BGRT radiotherapy, according to any of the methods described herein. The BGRT system (900) may comprise a gantry (902) rotatable about a patient area (904), one or more PET detectors (906) mounted on the gantry, a therapeutic radiation source (908) mounted on the gantry, and a dynamic multi-leaf collimator (910) disposed in the beam path of the therapeutic radiation source. In some variations, the BGRT system may comprise a first array of PET detectors (906a) and a second array of PET detectors (906b) disposed across from the first array, a linear accelerator (908) or linac, and a dynamic binary multi-leaf collimator (910). The system may further comprise a controller that is in communication with the gantry, PET detectors, linac, and MLC, where the controller has one or more memories that may store treatment plans, firing filters, fluence maps, system instructions/commands, and a processor configured to execute the calculations and methods described herein. A patient disposed within the patient area may have been injected with a PET tracer that emits positrons, and the PET tracer may accumulate at particular regions of the patient (e.g., irradiation-target regions such as tumor regions). In some variations, the PET tracer may have a targeting backbone that is the same as the targeting backbone of a radiopharmaceutical compound that will be injected in another treatment session as an internal therapeutic radiation source. The annihilation of a positron with a nearby electron may result in the emission of two photons traveling in opposite directions to define a line. One or more acquired PET partial images or detected PET partial image data may comprise one or more positron annihilation emission paths (i.e., lines of response or LORs, emission paths). In some variations, the PET detectors may be time-of-flight PET detectors, which may help to identify the location of the positron annihilation event. Optionally, BGRT system (900) may comprise a CT imaging system mounted on the same gantry as the therapeutic radiation source or mounted on a separate gantry. Additional details and examples of PET-based radiotherapy systems are described in U.S. patent application Ser. No. 15/814,222, filed Nov. 15, 2017 which is hereby incorporated by reference in its entirety.

Figure 10:
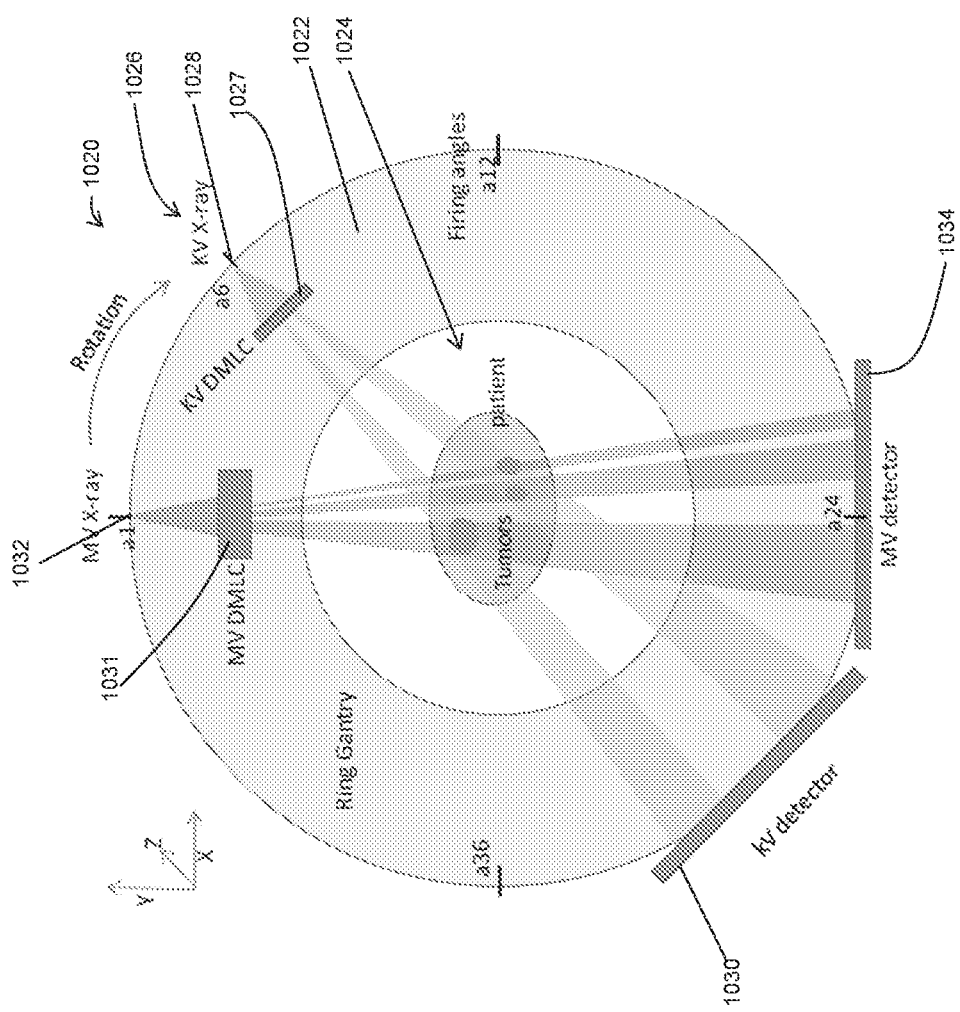
FIG. 10 depicts one variation of a radiotherapy system.

FIG. 10 depicts another variation of a radiotherapy system that may be used for external beam radiation therapy implementing any of the methods described herein. The radiotherapy system (1020) may comprise a gantry (1022) rotatable about a patient area (1024), a kV imaging system (1026) having a kV X-ray source (1028) and a kV detector (1030) mounted on the gantry, and a therapeutic radiation source (1032) (e.g., MV X-ray source) and a MV detector (1034) mounted on the gantry (1022). The kV detector (1030) may be located across the kV X-ray source (1028) and the MV detector (1034) may be located across the MV X-ray source (1032). Optionally, the kV imaging system may comprise a dynamic MLC (1027) over the kV X-ray source (1028). The system may comprise a dynamic MLC (1031) disposed over the MV X-ray source (1032). Partial images or imaging data may comprise image data acquired by the kV detector after each kV X-ray source pulse. Examples of partial kV X-ray images may include X-ray projection image data, such as 2D projection data. The kV imaging system may have a field-of-view that is co-planar or non-coplanar with the therapeutic radiation source irradiation field. The kV imaging system may be on the same or different gantry from the therapeutic radiation source. Additional details and examples of external beam radiotherapy systems are described in PCT/US18/25252, filed Mar. 29, 2018, which is hereby incorporated by reference in its entirety.

FIG. 11 depicts another variation of a radiotherapy system (1150) that may be used for external beam radiation therapy implementing any of the methods described herein. Radiotherapy system (1150) may comprise a gantry (1151) comprising a first pair of arms (1152) rotatable about a patient area and a second pair of arms (1154) rotatable about the patient area, an imaging system comprising a kV radiation source (1156) mounted on a first arm (1152a) of the first pair of arms (1152) and a kV detector (1158) mounted on a second arm (1152b) of the first pair of arms (1152), and a therapeutic radiation system comprising an MV radiation source (1160) mounted on a first arm (1154a) of the second pair of arms (1154) and an MV detector (1162) mounted on a second arm (1154b) of the second pair of arms (1154). The first and second arms of the first pair of arms (1152) may be located opposite each other (e.g., on opposite sides of the patient area, across from each other, and/or about 180 degrees from each other), such that the kV radiation source (1156) and the kV detector (1158) are located opposite each other (e.g., the kV detector is located in the beam path of the kV radiation source). The first and second arms of the second pair of arms (1154) may be located opposite each other (e.g., on opposite sides of the patient area, across from each other, and/or about 180 degrees from each other), such that the MV radiation source (1160) and the MV detector (1162) are located opposite each other (e.g., the MV detector is located in the beam path of the MV radiation source). Partial images or imaging data may comprise image data acquired by the kV detector after each kV X-ray source pulse. Examples of partial kV X-ray images may include X-ray projection image data, such as 2D projection data.

While various inventive variations and embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described variations and embodiments can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer (e.g., controller) or distributed among multiple computers (e.g., controllers).

Further, it should be appreciated that a computer or controller may be embodied in any of a number of forms, such as a rack-mounted computer, a desktop computer, a laptop computer, or a tablet computer. Additionally, a computer or controller may be embedded in a device not generally regarded as a computer but with suitable processing capabilities, including a Personal Digital Assistant (PDA), a smart phone or any other suitable portable or fixed electronic device.

Also, a computer or controller may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers or controllers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein (e.g., methods of joint radiotherapy treatment planning and joint optimization of ITRS radiation dose and ETRS radiation dose disclosed above) may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for joint internal and external radiotherapy, the method comprising:
   generating a radiotherapy treatment plan that specifies a radiation dose deliverable using an internal therapeutic radiation source (ITRS) and a radiation dose deliverable using an external therapeutic radiation source (ETRS), wherein the ITRS radiation dose and the ETRS radiation doses have been calculated by iterating through intermediate values of the ITRS radiation dose and intermediate values of the ETRS radiation dose to attain a cumulative radiation dose that meets prescribed dose requirements;
   delivering radiation in a first treatment session to a patient target region using a radiotherapy system comprising an ETRS movable about a patient target region; and
   delivering radiation in a second treatment session using an ITRS to the patient target region.

2. The method of claim 1, wherein generating the radiotherapy treatment plan comprises calculating the intermediate value of the ITRS radiation dose using functional image data.

3. The method of claim 2, wherein functional image data comprises PET data, CT data, SPECT data, or combinations thereof.

4. The method of claim 2, wherein the ITRS comprises an injectable compound and wherein calculating the intermediate value of the ITRS radiation dose uses biodistribution data derived from the functional image data.

5. The method of claim 1, wherein the prescribed dose requirements include one or more dose constraints.

6. The method of claim 5, wherein the one or more dose constraints comprises one or more cost functions.

7. The method of claim 6, wherein the one or more cost functions comprise a cost function on radiation toxicity to a non-target region.

8. The method of claim 6, wherein the one or more cost functions comprise a cost function on the ITRS radiation dose, ETRS radiation dose, or combinations thereof.

9. The method of claim 1, wherein the radiotherapy system further comprises a multi-leaf collimator disposed in a radiation beam path of the ETRS and a movable gantry upon which the ETRS is mounted, and wherein delivering radiation in the first treatment session comprises moving the gantry to position the ETRS at radiation emission locations and arranging leaves of the multi-leaf collimator at each of the radiation emission locations in order to deliver the ETRS radiation dose.

10. The method of claim 9, wherein the radiotherapy system further comprises a plurality of PET detectors, and wherein delivering radiation in the first treatment session comprises arranging leaves of the multi-leaf collimator and emitting radiation from the ETRS in response to PET detector data.

11. The method of claim 1, wherein delivering radiation in the second treatment session comprises injecting the ITRS into the patient, wherein the ITRS comprises a compound with a targeting backbone and a radionuclide.

12. The method of claim 11, wherein the targeting backbone is DOTA-TATE and the radionuclide is selected from a group consisting of Ga-68 and Lu-177.

13. The method of claim 11, wherein the targeting backbone is selected from the group consisting of DOTA-TOC, PSMA-11, PSMA-617, NeoBOMB1, Pentixafor, iobenguane (MIBG), TCMC trastuzumab, MDP, iodine, ibritumomab tiuxetan, SARTATE, thymidine, methionine, misonidazole (MISO), azomycin-arabinoside, erythronitroimidazole, a nitromidazole derivative, folic acid, 5F7 antibody, choline, DCFPyL, DCFBC, PD-1 binding protein, PD-L1 binding protein, PD-L2 binding protein, satoreotide tetraxetan, lexidronam, tositumomab, apamistamab, lilotomab satetraxetan, omburtamab, 3BP-227, fibroblast activation protein (FAP) inhibitor, FAP binding molecule, girentuximab and pentixather, and the radionuclide is selected from the group consisting of NaF-18, F-18, Ga-68, Cu-64, Zr-89, I-124, Sc-44, Tb-152, Y-86, Tc-99m, In-111, Tb-155, I-123, Cu-67, Sr-89, Y-90, I-131, Tb-161, Lu-177, Bi-212, Bi-213, At-211, Ac-225, Th-227, Ra-223, Pb-212, and Tb-149.

14. The method of claim 1, wherein delivering radiation in the second treatment session comprises implanting the ITRS at the patient target region, wherein the ITRS comprises a radioactive portion and a housing disposed over the radioactive portion.

15. The method of claim 14, wherein the implantable radiation source comprises a radioactive seed.

16. The method of claim 1, further comprising:
acquiring functional image data during the first treatment session using the ETRS; and
acquiring functional image data during the second treatment session using the ITRS.

17. The method of claim 16, further comprises calculating an updated ITRS radiation dose by calculating a radiation dose delivered in the second treatment session using the acquired functional image data from the second treatment session.

18. The method of claim 17, wherein calculating the updated ITRS radiation dose further comprises calculating a radiation dose delivered in the first treatment session.

19. The method of claim 18, wherein calculating a radiation dose delivered in the first treatment session uses the functional image data acquired from the first treatment session.

20. The method of claim 17, further comprising:
calculating an updated ETRS radiation dose,
wherein calculating the updated ITRS radiation dose and the updated ETRS radiation dose comprises
calculating an updated cumulative radiation dose by subtracting radiation doses delivered in the first and second treatment sessions;
iterating through intermediate values of ITRS radiation doses and intermediate values of ETRS radiation doses to attain the updated cumulative radiation dose; and
delivering the updated ITRS radiation dose using the ITRS in a third treatment session.

21. The method of claim 16, wherein acquiring functional image data comprises acquiring one or more PET image data, CT image data, MRI image data, SPECT image data, or combinations thereof.

22. The method of claim 1, wherein generating a radiotherapy treatment plan comprises:
acquiring functional image data using a first compound having a first targeting backbone and a first radionuclide; and
iterating through intermediate values of ITRS radiation doses and intermediate values of ETRS radiation doses that have been calculated based on the acquired functional image data,
wherein delivering radiation in the second treatment session uses an ITRS that comprises a second compound having a second targeting backbone and a second radionuclide.

23. The method of claim 22, wherein the first targeting backbone and the second targeting backbone are the same.

24. The method of claim 22, wherein the first radionuclide and the second radionuclide are the same.

25. The method of claim 22, wherein acquiring functional image data comprises acquiring one or more PET image data, CT image data, MRI image data, SPECT image data, or combinations thereof.

26. The method of claim 22, wherein the functional image data is acquired during a diagnostic imaging session.

27. The method of claim 22, wherein the functional image data is acquired during a previous treatment session using an ETRS of a radiotherapy system.

28. The method of claim 27, wherein the functional image data is acquired using an imager of the radiotherapy system.

* * * * *